US008852877B2

(12) United States Patent
Campbell et al.

(10) Patent No.: US 8,852,877 B2
(45) Date of Patent: Oct. 7, 2014

(54) APPARATUS AND METHOD FOR IDENTIFYING A HOOK EFFECT AND EXPANDING THE DYNAMIC RANGE IN POINT OF CARE IMMUNOASSAYS

(71) Applicant: Abbott Point of Care Inc., Princeton, NJ (US)

(72) Inventors: John Campbell, Woodlawn (CA); Linda Nguyen, Gloucester (CA); James Smith, North Gower (CA); Wenda Weiss, Munster (CA)

(73) Assignee: Abbott Point of Care Inc., Princeton, NJ (US)

( * ) Notice: Subject to any disclaimer, the term of this patent is extended or adjusted under 35 U.S.C. 154(b) by 0 days.

(21) Appl. No.: 14/141,837

(22) Filed: Dec. 27, 2013

(65) Prior Publication Data

US 2014/0186972 A1    Jul. 3, 2014

Related U.S. Application Data

(60) Provisional application No. 61/746,705, filed on Dec. 28, 2012.

(51) Int. Cl.
*G01N 33/53*    (2006.01)
*G01N 31/00*    (2006.01)
*G01N 33/543*    (2006.01)

(52) U.S. Cl.
CPC ............................... *G01N 33/54366* (2013.01)
USPC ........... 435/7.21; 435/7.1; 436/501; 436/518; 424/9.1; 424/520; 422/430; 530/300; 530/350

(58) Field of Classification Search
CPC ............. C07K 14/415; C07K 2299/00; C12N 15/8261; C12N 15/8271
See application file for complete search history.

(56) References Cited

U.S. PATENT DOCUMENTS

| | | | |
|---|---|---|---|
| 4,954,087 | A | 9/1990 | Lauks et al. |
| 5,096,669 | A | 3/1992 | Lauks et al. |
| 5,200,051 | A | 4/1993 | Cozzette et al. |
| 5,514,253 | A | 5/1996 | Davis et al. |
| 5,554,339 | A | 9/1996 | Cozzette et al. |
| 5,723,346 | A | 3/1998 | Frengen |
| 5,821,399 | A | 10/1998 | Zelin |
| 6,030,827 | A | 2/2000 | Davis et al. |
| 6,929,953 | B1 | 8/2005 | Wardlaw |
| 7,419,821 | B2 | 9/2008 | Davis et al. |
| 7,682,833 | B2 | 3/2010 | Miller et al. |
| 7,723,099 | B2 | 5/2010 | Miller et al. |
| 2001/0026920 | A1 | 10/2001 | Chandler et al. |
| 2003/0113713 | A1 | 6/2003 | Glezer et al. |
| 2003/0207290 | A1 | 11/2003 | Kenten et al. |
| 2004/0059519 | A1 | 3/2004 | Chandler et al. |
| 2004/0096985 | A1 | 5/2004 | Kenjiyou et al. |
| 2011/0105354 | A1 | 5/2011 | Glezer et al. |
| 2011/0206557 | A1 | 8/2011 | Phan et al. |
| 2012/0219457 | A1 | 8/2012 | Verrant et al. |
| 2013/0343955 | A1 | 12/2013 | Doyle et al. |

OTHER PUBLICATIONS

International Search Report and Written Opinion for PCT/US2013/077968 mailed Mar. 14, 2014.
U.S. Appl. No. 13/833,655, filed Mar. 15, 2013, Dowell.
Fernando, S. et al., "Studies of the 'hook' effect in the one-step sandwich immunoassay", Journal of Immunological Methods, 1992, pp. 47-46.

*Primary Examiner* — Lisa Cook

(57) ABSTRACT

The present invention relates to systems and methods for the rapid in situ determination of the existence of a hook effect and expansion of the dynamic range of a point of care immunoassay. For example, a system for identifying a hook effect and expanding the dynamic range of an immunoassay is provided that may include a primary sensor having first immobilized antibodies that may be configured to generate a first signal based on a presence or absence of a target analyte in a sample. The system may further include an attenuated sensor having second immobilized antibodies at a reduced concentration relative to a concentration of the first immobilized antibodies on the primary sensor and that may be configured to generate a second signal based on the presence or absence of the target analyte in the sample. The system may further include a processor configured to determine a presence of a hook effect in the immunoassay based on relative values of the first and second signals and optionally determine the target analyte concentration of the sample.

36 Claims, 18 Drawing Sheets

FIG. 1
Simultaneous Sandwich ELISA for bHCG
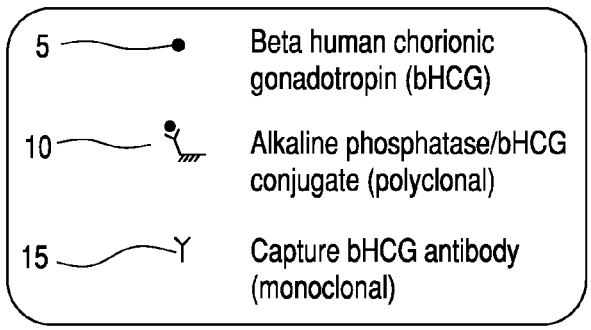
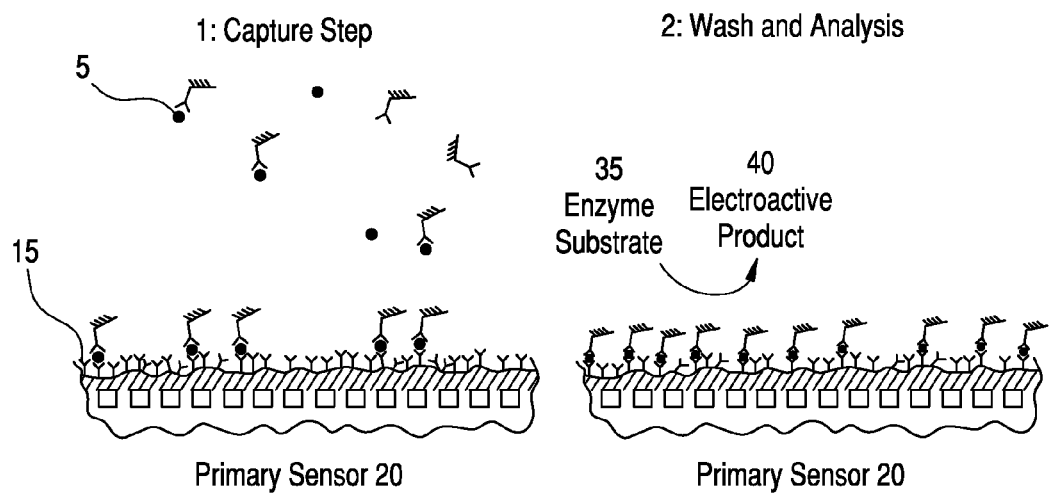
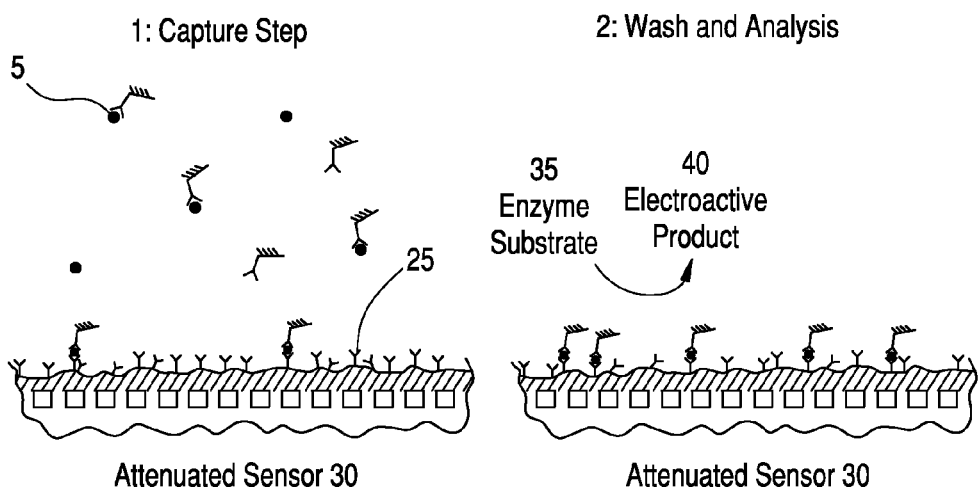

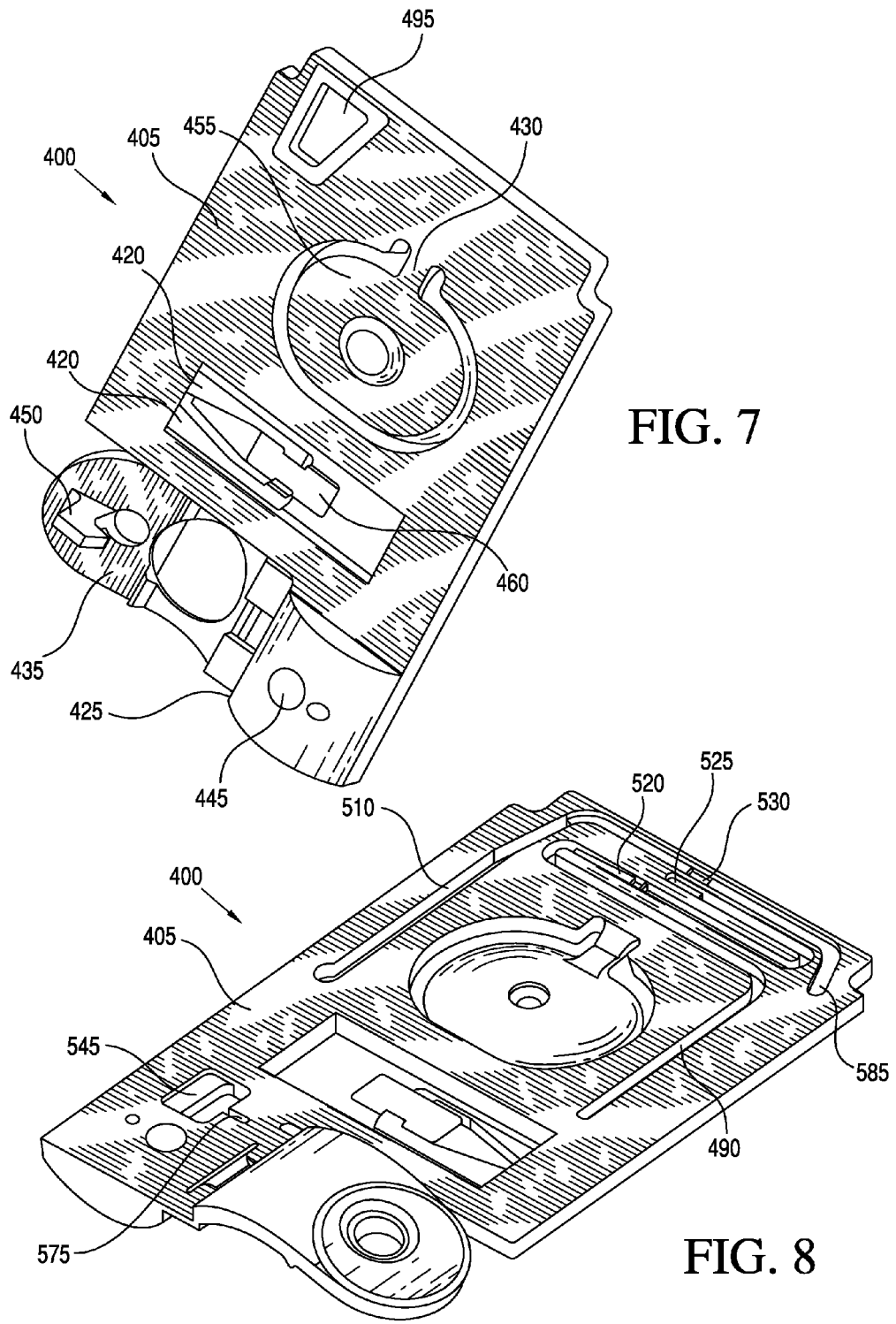

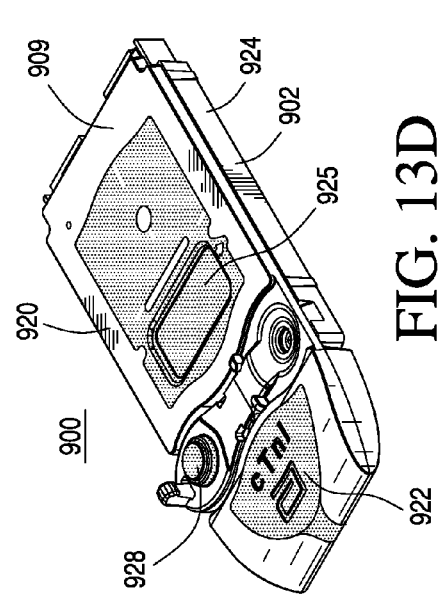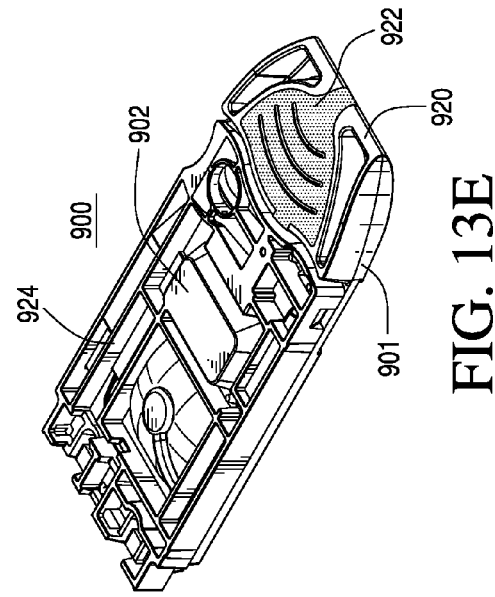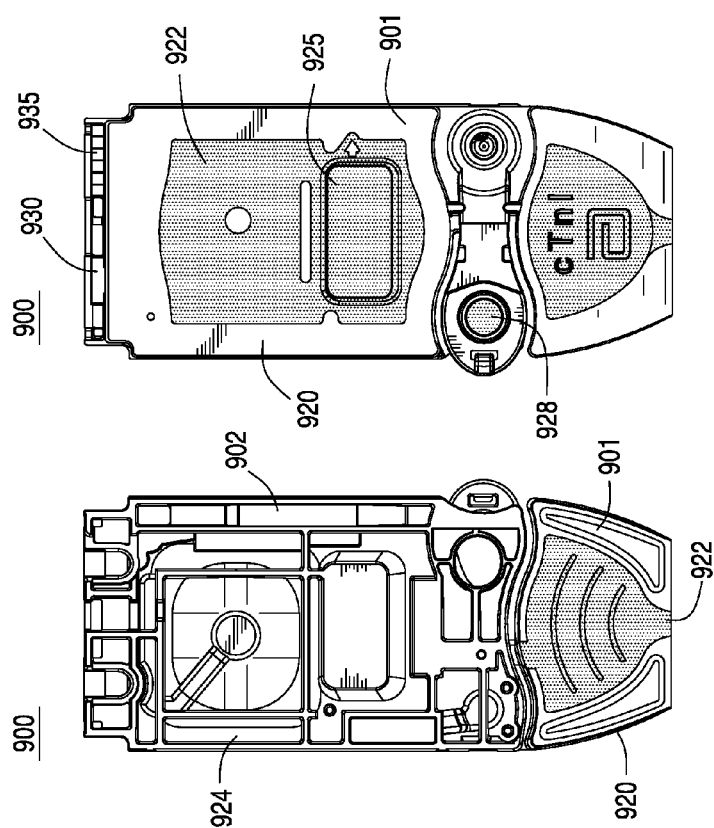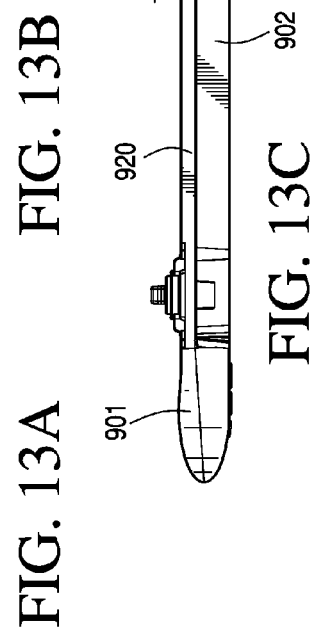

APPARATUS AND METHOD FOR IDENTIFYING A HOOK EFFECT AND EXPANDING THE DYNAMIC RANGE IN POINT OF CARE IMMUNOASSAYS

CROSS-REFERENCE TO RELATED APPLICATIONS

This is a non-provisional of Provisional Appl. 61/746,705, filed Dec. 28, 2012, the entirety of which is incorporated herein by reference.

FIELD OF THE INVENTION

The invention relates to analytical testing devices and methods of using same. Specifically, the invention relates to systems and methods for the rapid in situ determination of the existence of a hook effect and expanding the dynamic range in immunoassays, and in particular in point of care immunoassays.

BACKGROUND OF THE INVENTION

A multitude of laboratory tests for analytes of interest are performed on biological samples for diagnosis, screening, disease staging, forensic analysis, pregnancy testing, drug testing, and other reasons. While a few qualitative tests, such as pregnancy tests, have been reduced to simple kits for the patient's home use, the majority of quantitative tests still require the expertise of trained technicians in a laboratory setting using sophisticated instruments. Laboratory testing increases the cost of analysis and delays the results. In many circumstances, delay can be detrimental to a patient's condition or prognosis, such as for example the analysis of markers indicating myocardial infarction. In these critical situations and others, it would be advantageous to be able to perform such analyses at the point of care, accurately, inexpensively, and with a minimum of delay and with the assurance of the absence of a hook effect.

The hook effect, also known as a prozone effect, may arise in sandwich immunoassays when a sufficiently high concentration of a target analyte is present in the sample being tested. In particular, the high concentration of target analyte may result in substantially all of the signal antibody within the immunoassay binding to free analyte in the sample, and thus an insufficient amount of signal antibody remains to bind to analyte that is bound to the capture antibodies of the immunoassay. Consequently, a measured signal, e.g., at an immunosensor, is low, which is indicative of a small amount of analyte in the sample. However, in actuality, the analyte concentration is extremely high. The term hook effect comes from the observation that while the signal versus analyte response increases initially, e.g., in a quasi-linear fashion, the signal undesirably plateaus and then falls in a hook-like fashion.

Although a number of references disclose methods and systems for detecting the presence of the hook effect and ameliorating the affect in immunoassays, there remains a need for improved systems and methods for assuring the absence of the hook effect in immunoassays. In particular, the need remains for improved systems and methods for assuring the absence of the hook effect in immunoassay systems and methods that are intended for use outside the central laboratory, e.g., at the point of patient care. Accordingly, the need exists for ameliorating the hook effect impact on point-of-care analyte testing systems.

SUMMARY OF THE INVENTION

In one embodiment, the present invention is directed to a system for identifying a hook effect in an immunoassay. The system includes a primary sensor comprising first immobilized antibodies that is configured to generate a first signal based on a presence or absence of a target analyte in a sample. The system further includes an attenuated sensor comprising second immobilized antibodies at a reduced concentration relative to a concentration of the first immobilized antibodies on the primary sensor and that is configured to generate a second signal based on the presence or absence of the target analyte in the sample. The system also includes a processor configured to determine a presence of a hook effect in the immunoassay based on relative values of the first and second signals.

In some aspects, the first and second immobilized antibodies may be immobilized on microparticles. The microparticles may be adsorbed over the primary sensor and the attenuated sensor. In some embodiments, the microparticles adsorbed over the attenuated sensor may comprise the second immobilized antibodies and a co-absorbate, and the microparticles adsorbed over the primary sensor may not comprise the co-absorbate. The co-absorbate dilutes surface activity of the second immobilized antibodies on the microparticles adsorbed over the attenuated sensor.

In some embodiments, the system further comprises at least one additional sensor comprising third immobilized antibodies at a different concentration relative to the concentrations of the first and second immobilized antibodies on the primary and attenuated sensors, respectively, and that is configured to generate a third signal based on the presence or absence of the target analyte in the sample. The processor is further configured to determine a concentration of the target analyte based on the presence of the hook effect and relative values of the first, second, and third signals.

In another embodiment, the present invention is directed to an immunosensor system for identifying a hook effect in an immunoassay. The system includes a primary immunosensor comprising a first immobilized antibody configured to generate a first signal based on a sandwich between the first immobilized antibody, a target analyte, and a labeled antibody. The system further includes an attenuated immunosensor comprising a second immobilized antibody at a reduced concentration relative to a concentration of the first immobilized antibody on the primary immunosensor and that is configured to generate a second signal based on a sandwich between the second immobilized antibody, the target analyte, and the labeled antibody. The system also includes a processor configured to determine a presence of a hook effect in the immunoassay based on relative values of the first and second signals.

In some embodiments, the labeled antibody may be labeled with alkaline phosphatase (ALP) and the first and second signals may be generated at the primary immunosensor and the attenuated immunosensor respectively from an electroactive species with a phosphate moiety that is cleaved by the ALP.

In some aspects, the primary immunosensor and the attenuated immunosensor may be disposed in a disposable cartridge that is configured to perform the immunoassay to determine a presence of the target analyte in a sample. The target analyte optionally may be selected from the group consisting of: troponin I, troponin T, creatine kinase myocardial band (CKMB), procalcitonin, beta human chorionic gonadotropin (bHCG), human chorionic gonadotropin (HCG), N-terminal pro brain natriuretic peptide (NTproBNP), pro brain natriuretic peptide (proBNP), brain natriuretic peptide (BNP), myoglobin, parathyroid hormone, d-dimer, neutrophil gelatinase-associated lipocalin (NGAL), galectin-3, and prostate specific antigen (PSA).

In another embodiment, the present invention is directed to an immunosensor system comprising a plurality of immunosensors. Each immunosensor of the plurality of immunosensors comprises a different concentration of an immobilized antibody specific to an analyte of interest, and each immunosensor is configured to generate a signal based on a sandwich between the immobilized antibody, the analyte of interest, and a labeled antibody. The system further comprises a processor configured to determine the presence of a hook effect in an immunoassay based on relative values of each generated signal.

In some aspects, the processor may be further configured to determine a concentration of the analyte of interest based on the presence of the hook effect and the relative values of each generated signal.

In another embodiment, the present invention is directed to a method for identifying a hook effect in an immunoassay. The method comprises providing a sample to a primary sensor comprising first immobilized antibodies, generating a first signal from the primary sensor based on a presence or absence of a target analyte in the sample, and providing the sample to an attenuated sensor comprising second immobilized antibodies provided at a reduced concentration relative to a concentration of the first immobilized antibodies on the primary sensor. The method further comprises generating a second signal from the attenuated sensor based on the presence or absence of the target analyte in the sample, determining a ratio of the first and the second signals based on relative values of the first and second signals, and determining the presence or absence of a hook effect in the immunoassay based on the determined ratio.

In yet another embodiment, the present invention is directed to a method of using an attenuated immunosensor for identifying a hook effect in an immunoassay for a target analyte. The method comprises applying a sample to a primary immunosensor comprising a first immobilized antibody, generating a first signal from the primary immunosensor based on a sandwich between the first immobilized antibody, the target analyte, and a labeled antibody, and applying the sample to the attenuated immunosensor comprising a second immobilized antibody provided at a reduced concentration relative to a concentration of the first immobilized antibody on the primary immunosensor. The method further comprises generating a second signal from the attenuated immunosensor based on a sandwich between the second immobilized antibody, the target analyte, and the labeled antibody, computing relative values of the first and second signals, determining a ratio of the first and second signals based on the relative values of the first and second signals, and determining a presence or absence of a hook effect in the immunoassay based on the determined ratio.

BRIEF DESCRIPTION OF THE DRAWINGS:

The present invention will be better understood in view of the following non-limiting figures, in which:

FIG. 1 illustrates the principle of operation of a primary sensor and an attenuated sensor in accordance with some aspects of the invention;

FIG. 7 shows an isometric top view of an immunosensor cartridge cover in accordance with some aspects of the invention;

FIG. 8 shows an isometric bottom view of an immunosensor cartridge cover in accordance with some aspects of the invention;

FIGS. 13A-13E show top, bottom, side, and perspective views of an immunosensor cartridge in a closed position in accordance with some aspects of the invention;

DETAILED DESCRIPTION OF THE INVENTION

Introduction

Figure 2:
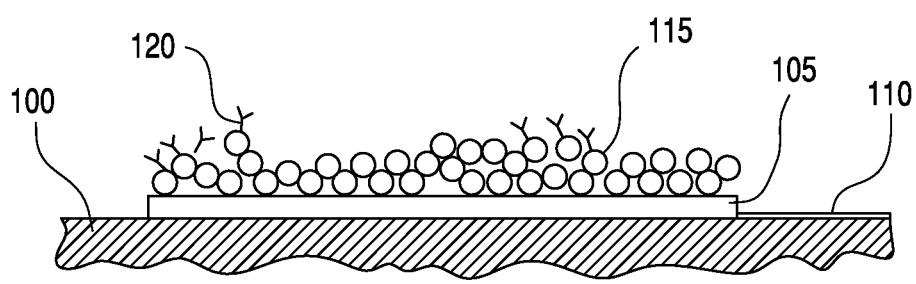
FIG. 2 shows a side view of the fabrication of an immunosensor in accordance with some aspects of the invention.

The present invention relates generally to immunoassay technology and concerns the attenuation of sensitivity in antibody reagents for immunosensors allowing tuning of a signal response function. More specifically, the present invention relates to point of care immunoassay technologies and concerns the attenuation of sensitivity in antibody-coated microparticle reagents for printing on sensors allowing tuning of the signal response function. Preferred embodiments of the present invention may be implemented using at least one analyte-detecting sensor (e.g., a primary immunosensor) and at least one attenuated sensor (e.g., an attenuated immunosensor) that may be configured to function as a detector of the hook effect in an immunoassay. In accordance with a preferred embodiment, such systems and methods also may be employed to expand the linear dynamic range of the immunoassays.

Some aspects of the present invention are configured for rapid in situ determinations of analytes using a cartridge, preferably a disposable cartridge, having an array of sensors (e.g., a pair of immunosensors comprising the primary sensor and the attenuated sensor) and a means for sequentially or substantially sequentially presenting a sample and a fluid (amended or not amended) to the sensor array. The cartridges may be configured to be preferably operated with a reading device, such as the reading devices disclosed in U.S. Pat. Nos. 5,096,669, 5,821,399, and 7,419,821, which are incorporated herein by reference in their entireties. Details of the cartridge and reader device utilized in accordance with these aspects of the present invention are described below in further detail.

One embodiment of the invention, therefore, provides a single-use or disposable cartridge with a sample-holding chamber connected to a first conduit that contains both the primary sensor and the attenuated sensor. A second conduit, partly containing a fluid, optionally derived from a burstable pouch, may be connected to the first conduit, and air segments may be introduced into the fluid in the second conduit in order to segment the fluid. A pump may be provided within the cartridge. The pump may be configured to displace the sample within the first conduit, and displace a second fluid from the second conduit into the first conduit. Thus, the pair of immunosensors may be contacted first by the sample and subsequently by the second fluid.

In a second embodiment, the cartridge is provided with a closeable valve located between the first conduit and a waste chamber. This embodiment permits displacement of the fluid from the second conduit into the first conduit using only a single pump connected to the first conduit. This embodiment further permits efficient washing of the first and the second conduits of the cartridge. During operation of the cartridge, the sample may be displaced to contact the pair of immunosensors, and may then be displaced through a closeable valve into the waste chamber. Upon wetting the closable valve by the sample, the closeable valve seals the opening to the waste chamber, providing an airtight seal that allows fluid in the second conduit to be drawn into contact with the pair of immunosensors using the pump connected to the first conduit. In this embodiment, the closeable valve permits the fluid to be displaced and prevents air from entering the first conduit from the waste chamber.

In a third embodiment, both a closeable valve and means for introducing air segments into a conduit are provided. Advantageously, this configuration provides for the ability to reciprocate a segmented fluid over the pair of immunosensors. Thus, a first segment of air or set of segments of air may be used to facilitate rinsing of the pair of immunosensors. A fresh segment of air may then be positioned over the pair of immunosensors for taking measurements. In this embodiment, only one pump (that connected to the conduit) may be required for operation of the cartridge.

In a fourth embodiment, analyte measurements are performed in a thin-film of liquid that is coating the pair of immunosensors. The thin-film determination may preferably be performed amperometrically. This embodiment differs from the foregoing embodiments in having both a closeable valve that is sealed when the sample is expelled through the valve, and an air vent within the conduits that permits at least one air segment to be subsequently introduced into the measuring fluid. Advantageously, this configuration may increase the efficiency with which the sample is rinsed from the pair of immunosensors, and may further permit removal of substantially all of the fluid from the pair of immunosensors prior to measurement. Even more advantageously, this configuration may permit segments of fresh liquid to be brought across the pair of immunosensors to permit sequential, repetitive measurements for improved accuracy and internal checks of reproducibility.

In preferred embodiments, an analysis scheme for the detection of low concentrations of immunoactive analyte may rely on the formation of an enzyme labeled sandwich complex. A concentration of analyte in a sample may be converted into a proportional surface concentration of the enzyme. The enzyme may be capable of amplifying the analyte chemical signal by converting the substrate to a detectable product. For example, where alkaline phosphatase (ALP) is the enzyme, a single enzyme molecule can produce about nine thousand detectable molecules per minute, providing several orders of magnitude improvement in the detectability of the analyte compared to schemes in which an electroactive species is attached to the antibody in place of ALP.

In the present embodiments, it may be advantageous to contact the pair of immunosensors first with a sample and then with a wash fluid prior to recording a response from the sensors. In specific embodiments, the sample may be amended with an antibody-enzyme conjugate that binds to the analyte of interest within the sample before the amended sample contacts a pair of immunosensors. Binding reactions in the sample produce an analyte/antibody-enzyme sandwich complex. The primary immunosensor may comprise an immobilized antibody to the analyte, attached close to an electrode surface. Upon contacting the primary immunosensor, the analyte/antibody-enzyme complex binds to the immobilized antibody near the electrode surface. This same reaction may occur at an attenuated immunosensor (e.g., the hook-detecting sensor) that may be located adjacent to or remote from the primary immunosensor.

At this point it may be advantageous to remove as much of the unbound antibody-enzyme conjugate as possible from the vicinity of the electrodes to minimize background signal from the sensors. The enzyme of the antibody-enzyme complex may be configured to convert a substrate, provided in the fluid, to produce an electrochemically active species. This active species may be produced close to each electrode and may provide a current from a redox reaction at the electrode when a suitable potential is applied (amperometric operation). Alternatively, if the electroactive species is an ion, it may be measured potentiometrically. In amperometric measurements, the potential may either be fixed during the measurement, or varied according to a predetermined waveform. For example, a triangular wave can be used to sweep a potential between limits, as is used in the well-known technique of cyclic voltammetry. Alternatively, digital techniques such as square waves can be used to improve sensitivity in detection of the electroactive species adjacent to the electrode. From the current or voltage measurement, an amount or presence of the analyte in the sample may be calculated.

In embodiments in which the cartridge comprises the pair of immunosensors, the immunosensors may be microfabricated from a base sensor of an unreactive metal such as gold, platinum or iridium, and a porous permselective layer which is overlaid with a bioactive layer attached to a microparticle, for example latex particles. The microparticles may be dispensed onto the porous layer covering the electrode surface, forming an adhered, porous bioactive layer. The bioactive layer may have the property of binding specifically to the analyte of interest, or of manifesting a detectable change when the analyte is present, and is most preferably an immobilized antibody directed against the analyte. The essential difference between the immunosensor directed primarily to quantitation of the analyte and the attenuated immunosensor is the relative loading of the capture antibody or immobilized antibody.

In operation, therefore, one goal of the present invention is to provide a dual immunosensor cartridge that is preferably operated as follows. An unmetered amount of a preferably biological sample is placed into the sample chamber of the cartridge, and the cartridge is placed into a reading apparatus. A metered portion of the sample is amended with at least one antibody-enzyme conjugate, and is then contacted with the two immunosensors. A second fluid, which contains an electro-inactive substrate for the enzyme, is used to rinse the immunosensors substantially free of unbound antibody-enzyme conjugate, and the electrical response of the two immunosensors is recorded and analyzed for the presence, or amount of, the analyte of interest and/or the presence of a hook effect.

Hook Detection

The general concept for hook detection in the present invention is based on differential measurement between at least two sensors, e.g., the primary sensor and the attenuated sensor. Specifically in some aspects of the present invention, hook detection may be based on the comparison of relative values of a first signal generated from a primary amperometric electrochemical immunosensor and a second signal generated from an attenuated amperometric electrochemical immunosensor. However, it should be understood that while differential measurement is described herein based on pairs of amperometric electrochemical immunosensors, differential measurement for hook detection may be of equal utility in other electrochemical sensing systems including potentiometric sensors, field effect transistor sensors, and conductimetric sensors. Moreover, differential measurement for hook detection may also be applicable to optical sensors, e.g., evanescent wave sensors and optical wave guides, and other types of sensing including acoustic wave and thermometric sensing and the like.

In preferable embodiments, the first signal generated from the primary sensor (e.g., a first amperometric electrochemical immunosensor) may be derived from formation of a sandwich between an immobilized antibody (e.g., the immobilized antibody may be attached to microparticles), a target analyte or antigen, and a signal antibody (e.g., the signal antibody may be labeled). For example, the target analyte from a sample may bind with the immobilized antibody, and then the signal antibody may bind to the target analyte to form the sandwich. The label (e.g., an enzyme such as alkaline phosphatase) attached to the signal antibody may react with a substrate to form a detectable product that is indicative of a concentration of the captured analyte within a sample. The detectable product causes an electrical potential to be generated across the primary sensor that in turn generates the first signal relative to the electrical potential caused by the detectable product.

However, as described above, there is the possibility that the first sensor generates an artificially low signal indicative of a low concentration of the captured analyte in the sample in circumstances where the target analyte concentration is actually extremely high within the sample, e.g., in instances where the primary sensor is exhibiting the hook effect. In such cases, a second attenuated immunosensor may be utilized (e.g., a second attenuated amperometric electrochemical immunosensor may be placed in the cartridge) that effectively acts as a hook detector using differential measurements between the primary sensor and the attenuated sensor. The second signal generated from the attenuated sensor (e.g., a second attenuated amperometric electrochemical immunosensor) may be derived from formation of a sandwich between an immobilized antibody (e.g., the immobilized antibody may be attached to microparticles at a reduced concentration as compared to the first or primary sensor), the target analyte or antigen, and the signal antibody (e.g., the signal antibody may be labeled). For example, the target analyte from a sample may bind with the immobilized antibody, and then the signal antibody may bind to the target analyte to form the sandwich. The label (e.g., an enzyme such as alkaline phosphatase) attached to the signal antibody may react with the substrate to form the detectable product. The detectable product causes an electrical current to be generated at the attenuated sensor, which is compared to the first signal at the first sensor. Accordingly, the first signal from the primary sensor assures the sensitivity of the immunoassay and the second signal from the attenuated sensor expands the dynamic range of the immunoassay.

A processor within the cartridge and/or the reader device may be configured to compare the first signal from the primary sensor to the second signal from the attenuated sensor to determine the presence of the hook effect and quantify a concentration of the target analyte within the sample, as discussed in further detail below. Therefore, in accordance with some aspects of the present invention, tailoring the concentration of the immobilized antibody on the attenuated sensor provides the ability to both detect the presence of the hook effect and quantify a concentration of the target analyte.

Without being bound by theory, ideally the response for the first or primary sensor decreases after an optimum response (i.e., the hook effect) is achieved, because the large excess of analyte drives the equilibrium in the reverse direction, favoring formation of solution phase analyte antibody complexes. However, it is has been observed that if the capture antibody (e.g., the solid phase) concentration is increased, the optimum response shifts to higher analyte concentrations as the capacity of the capture antibody is increased. For example, if the concentration of the capture antibody is increased by a certain factor an ideal high-dose plateau (e.g., a normalized response) may be achieved because of the high capacity of the capture antibody. This substantiates the validity of sensitivity of dose response to capacity/concentration of the capture antibody (e.g., the solid phase), and thus the capability to both detect the presence of the hook effect and quantify the target analyte based on the observed dose response between the primary sensor and the attenuated sensor.

In a preferred embodiment, the present invention comprises an amperometric electrochemical system comprising the primary sensor and the attenuated sensor. The primary sensor and the attenuated sensor may be configured to detect an electrical current or potential associated with the oxidation of p-aminophenol (e.g., generated by the action of the enzyme alkaline phosphatase (ALP) on the substrate p-aminophenyl phosphate) generated across or near a surface of the primary sensor and the attenuated sensor. The primary sensor and the attenuated sensor may be further configured to generate the first and the second signals respectively based on the electrical current detected across or near the surface of the immunosensors, and the first and the second signals may be recorded by the analyzer device. In one embodiment, the potentials at both of the sensors may be set at a same value with respect to a silver-silver chloride reference electrode (or measured with respect to this reference electrode).

FIG. 1 illustrates the principle of this amperometric electrochemical system with integral hook detection according to specific embodiments of the present invention for determination of beta human chorionic gonadotropin (bHCG) 5, a marker for pregnancy. However, it should be understood that while the preferred embodiment is described for a bHCG assay, the sensor structure and microparticle reagents described herein may also be useful for detecting troponin I, troponin T, creatine kinase myocardial band (CKMB), procalcitonin, beta human chorionic gonadotropin (bHCG), human chorionic gonadotropin (HCG), N-terminal pro brain natriuretic peptide (NTproBNP), pro brain natriuretic peptide (proBNP), brain natriuretic peptide (BNP), myoglobin, parathyroid hormone, d-dimer, neutrophil gelatinase-associated lipocalin (NGAL), galectin-3, and/or prostate specific antigen (PSA), among other analytes.

In a capture step, a sample, e.g., blood or urine, may be introduced into a sample holding chamber of the cartridge of the present invention, and may be amended by a conjugate molecule 10 comprising ALP (e.g., an enzyme) covalently attached to a polyclonal anti-bHCG (e.g., a signal antibody). For example, the sample may be mixed with a dry reagent comprising the conjugate molecule 10 bound to a surface of a conduit or the sample holding chamber of the cartridge.

The conjugate molecule 10 may specifically bind to the bHCG 5, in the sample, producing a complex comprising the bHCG 5 bound to the ALP-bHCG conjugate molecule 10. In a capture step, the complex comprising the bHCG 5 bound to the ALP-bHCG conjugate molecule 10 may bind to a capture bHCG antibody 15 (e.g., an immobilized antibody) attached on, or close to, the primary sensor 20. Additionally, the complex may bind to capture bHCG antibody 25 attached on, or close to, the attenuated sensor 30 (e.g., an attenuated solid phase by virtue of the attenuated sensor 30 bearing a lower coverage/capacity of the same antibody as attached to the primary sensor 20). Accordingly, the primary sensor 20 and the attenuated sensor 30 may be coated with a biolayer comprising the covalently attached capture bHCG antibody 15 and the capture bHCG antibody 25, respectively, to which the complex comprising the bHCG 5 bound to the ALP-bHCG conjugate molecule 10 is bound. The ALP is thus immobilized on or in close proximity to each sensor.

A capture region on each sensor comprising the capture bHCG antibody 15 and/or the capture bHCG antibody 25 may be defined by a hydrophobic ring of polyimide or another photolithographically produced layer. A microdroplet or several microdroplets (approximately 5-40 nanoliters in size) containing antibodies in some form, for example bound to latex microparticles, may be dispensed on the surface of each sensor. The photodefined ring contains this aqueous droplet allowing the antibody coated region to be localized to a precision of a few microns. The capture region may be made from about 0.03-2 mm$^2$ in size. The upper end of this size (e.g., 2 mm$^2$) may be limited by a size of a sensor conduit comprising the sensors in present embodiments, and is not a limitation of the invention.

In addition to specific binding, the complex comprising the bHCG 5 bound to the ALP-bHCG conjugate molecule 10 may also bind non-specifically to the sensor. Non-specific binding may introduce a background signal from the sensors that is undesirable, and preferably should be minimized. Accordingly, in a rinsing step, a rinsing protocol that utilizes a segmented fluid to rinse the sensors may provide an efficient means to minimize the background signal. In an analysis step subsequent to the rinsing step, a substrate 35 that is hydrolyzed by, for example, ALP to produce a detectable electroactive product 40 may be introduced to the sensors. In specific embodiments, the substrate 35 may be comprised of p-aminophenylphosphate.

Thereafter, the ALP attached to the complex reacts with the substrate 35 to form the detectable product 40 that may be indicative to a concentration of the captured bHCG 5 within the sample. The detectable product 40 causes an electrical potential to be generated across the primary sensor 20 that in turn generates the first single relative to the electrical potential caused by the detectable product 40. In the absence of a hook effect, the detectable product 40 generated from the reaction of the ALP with the substrate 35 at the primary sensor 20 may be essentially proportional to an amount of bHCG 5 initially present in the sample.

An analogous reaction may occur at the attenuated sensor 30. Specifically, the detectable product 40 causes an electrical potential to be generated across the attenuated sensor 30 that in turn generates the second single relative to the electrical potential caused by the detectable product 40. In accordance with some aspects of the invention, data may be recorded by the analyzer device from the two sensors that may be used to detect enzymatically produced p-aminophenol generated from a reaction of the p-aminophenylphosphate with the enzyme label comprising ALP. The two sensors may be clamped at a fixed electrochemical potential sufficient to oxidize or reduce p-aminophenol from the hydrolyzed p-aminophenylphosphate, but not the p-aminophenylphosphate directly, or the potential may be swept one or more times through an appropriate range. In accordance with alternative or additional embodiments of the present invention, other species with phosphate groups may be used to generate the electroactive species detected by the two sensors, e.g., various ferrocenes with phosphate moieties.

In some embodiments, the substrate 35 may comprise a p-aminophenol species, and may be selected such that a voltammetric half-wave potential ($E_{1/2}$) of the substrate 35 and the detectable electroactive product 40 differ substantially. Preferably, the $E_{1/2}$ of the substrate 35 is substantially higher (more positive) than that of the product 40. For example, when the $E_{1/2}$ of the substrate 35 is substantially higher (more positive) than that of the product 40, the product 40 can be selectively electrochemically measured in the presence of the substrate.

The detection of ALP activity in above example relies on a measurement of the p-aminophenol oxidation current. This is achieved at a potential of about +60 mV versus the Ag/AgCl ground chip. The exact form of detection used depends on the sensor configuration. In one embodiment of the sensor, an array of gold microelectrodes may be located directly beneath the antibody capture region (e.g., the biolayer). When the analysis fluid is pulled over the array of gold microelectrodes, enzyme located on the capture site converts the p-aminophenylphosphate to p-aminophenol in an enzyme-limited reaction. The concentration of the p-aminophenylphosphate may be selected to be in excess, e.g., 10 times the Km value. The analysis solution is 0.1 M in diethanolamine, 1.0 M NaCl, buffered to a pH of 9.8. Additionally, the analysis solution may comprise 0.5 mM MgCl, which is a cofactor for the enzyme. Alternatively, a carbonate buffer has the desired properties and may be included in the analysis fluid.

In alternative embodiments, the enzyme conjugated to an antibody or other analyte-binding molecule may be urease, and the substrate may be urea. Ammonium ions produced by the hydrolysis of urea are detected in this embodiment by the use of an ammonium sensitive electrode. Ammonium-specific electrodes are well known to those of skill in the art. A suitable microfabricated ammonium ion-selective electrode is disclosed in U.S. Pat. No. 5,200,051, which is hereby incorporated by reference in its entirety. Other enzymes that react with a substrate to produce an ion are known in the art, as are other ion sensors for use therewith.

Fabrication of the Primary and Attenuated Sensors

Preferred embodiments of a microfabricated sensor array comprising the primary and the attenuated sensors are shown in FIG. 2. In the preferred embodiments, the attenuated sensor may be the same in all significant respects (e.g., dimensions, porous screening layer, latex particle coating, and metal electrode composition) as the primary sensor except that the capture or microparticle reagent for the target analyte (e.g., the biolayer) is present in an attenuated form, e.g., having a lower concentration of immobilized antibody relative to the immobilized antibody concentration in the primary sensor. For example, the primary sensor and the attenuated sensor may be fabricated as adjacent or remote structures, respectively, on a silicon chip.

In the preferred embodiments, the sensors may be formed with gold surfaces coated with a photodefined layer of polyimide. For example, wafer-level microfabrication of a preferred embodiment of the sensor array may be achieved as follows. A planar non-conducting substrate 100 may be used as a base for the sensor array. A conducting layer 105 may be deposited on the substrate 100 by conventional means or microfabrication known to those of skill in the art to form at least one electrode. The conducting layer 105 may comprise a noble metal such as gold or platinum, although other unreactive metals such as iridium may also be used, as many non-metallic electrodes of graphite, conductive polymer, or other materials may also be used.

For example, a base electrode may comprise a square array of 5-10 μm gold disks, e.g., 7 μm gold disks, on 15 μm centers. The array may cover a region, e.g., a circular region, approximately 300 to 900 μm in diameter, optionally 600 μm in diameter, and may be formed by photo-patterning a thin layer of the polyimide of thickness 0.35 μm over a substrate made from a series of layers comprising Si,$SiO_2$,TiW, and/or Au, or combinations thereof The array of microelectrodes affords high collection efficiency of electroactive species with a reduced contribution from any electrochemical background current associated with the capacitance of the exposed metal. In particular, regularly spaced openings in the insulating polyimide layer define a grid of small gold electrodes at which the p-aminophenol may be oxidized in a 2electron per molecule reaction.

Microfabrication techniques (e.g. photolithography and plasma deposition) may be utilized for construction of the multilayered sensor structures in confined spaces. For example, methods for microfabrication of the electrochemical immunosensors on silicon substrates are disclosed in U.S. Pat. No. 5,200,051, which is hereby incorporated by reference in its entirety. These include dispensing methods, methods for attaching biological reagent, e.g., antibodies, to surfaces including photoformed layers and microparticle latexes, and methods for performing electrochemical assays.

The microfabricated sensor array may also comprise an electrical connection 110 and a biolayer 115 (as discussed above with respect to FIG. 1), which are deposited onto at least a portion of the conducting layer 105 and/or the non-conducting substrate 100. In the present invention, the biolayer 115 may include a porous layer comprising a surface with a sufficient amount of a molecule 120 (e.g., the immobilized antibody and/or the microparticle reagent) that may either bind to an analyte of interest, or respond to the presence of such an analyte by producing a change that is capable of measurement.

In specific embodiments, the biolayer 115 may be formed from latex beads of specific diameter in the range of about 0.01 to 5.0 μm. The beads may be modified by covalent attachment of any suitable molecule consistent with the above definition of the biolayer (as discussed in further detail below). Many methods of attachment exist in the art, including providing amine reactive N-hydroxysuccinimide ester groups for the facile coupling of lysine or N-terminal amine groups of proteins. In specific embodiments, the molecule is an antibody selected to bind one or more of troponin I, troponin T, CKMB, procalcitonin, bHCG, HCG, NTproBNP, proBNP, BNP, myoglobin, parathyroid hormone, d-dimer, NGAL, galectin-3, PSA, or modified fragments thereof Such modified fragments are generated by oxidation, reduction, deletion, addition or modification of at least one amino acid, including chemical modification with a natural moiety or with a synthetic moiety. Preferably, the molecule binds to the analyte specifically and has an affinity constant for binding analyte ligand of about $1\times10^{-7}$ to $1\times10^{-15}$.

In one embodiment, the biolayer 115 comprising microparticle beads having surfaces that are covalently modified by a suitable molecule, may be affixed to the sensors by the following method. A microdispensing needle may be used to deposit onto a surface of the sensors a small droplet, preferably about 20 nL, of a suspension of modified beads. The droplet may be permitted to dry, which results in a coating of the beads on the surface that resists displacement during use.

Optionally, a permselective screening layer may be interposed between the conducting layer 105 and the biolayer 115 to screen electrochemical interferents as described in U.S. Pat. No. 5,200,051. In particular, the primary sensor and the attenuated sensor described herein may be manufactured to optimize a signal-to-noise ratio, or amperometric background signal. For example, an intervening polyvinyl alcohol (PVA) layer of about 0.5-5.0 μm thickness (preferably 0.6-1.0 μm) may be placed between the electrodes and the biolayer or antibody reagent layer significantly attenuating the background component, as described in U.S. Pat. No. 7,723,099, which is hereby incorporated by reference in its entirety. An advantage of PVA as the background-reducing layer is that noise is reduced without appreciably affecting the Faradaic component of the signal. While the PVA layer reduces the diffusion coefficient of small molecules by about 50% it has been found that it does not change the current at the coated electrodes, for two reasons. First, with PVA layers of about 1 micron thickness, the detected electroactive species is present in a diffusion layer of at least ten times that thickness, so there is little decrease in transport due to the PVA layer. Second, a steady-state current is measured in the immunosensor, which is effectively independent of the transport rate and electrode kinetics, but is a function of the enzymatic rate of production of the detectable species, such as p-aminophenol generated from p-aminophenylphosphate by the enzyme ALP (attached to the signal antibody).

The porous PVA layer may be prepared by spin-coating an aqueous mixture of PVA plus a stilbizonium photoactive, cross-linking agent over the microelectrodes on the wafer. The spin-coating mixture optionally includes bovine serum albumin (BSA). The spin-coating mixture may then be photo-patterned to cover only a region above and around the sensor arrays, and preferably has a thickness of about 0.6 μm.

Figure 3:
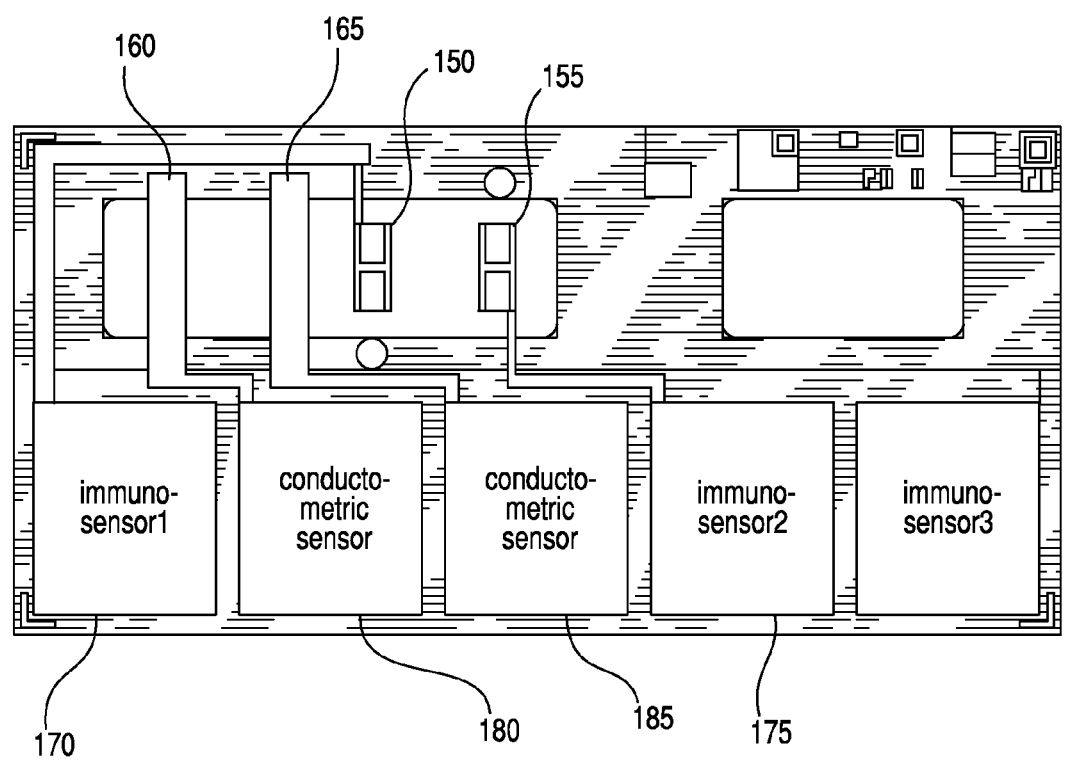
FIG. 3 shows a top view of a mask design for conductimetric and immunosensor electrodes in accordance with some aspects of the invention.

Referring to FIG. 3, a mask design for several electrodes upon a single substrate is illustrated. By masking and etching techniques, independent electrodes and leads may be deposited. Thus, a plurality of sensors 150 and 155 (e.g., the primary sensor and the attenuated sensor), and conductimetric sensors 160 and 165 may be provided in a compact area of the cartridge at low cost, together with respective connecting pads 170, 175, 180, and 185, for effecting electrical connection to the reading device. In principle, a very large array of sensors may be assembled in this way, each sensitive to a different analyte or acting as a control sensor or reference sensor. As described above, the primary sensor and the attenuated sensor may further comprise a biolayer, while the reference sensor may be constructed, for example, from gold electrodes lacking a biolayer, or from silver electrodes, or other suitable material. Different biolayers can provide each sensor with the ability to sense a different analyte.

In a preferred embodiment of the present invention, the plurality of sensors 150 and 155 may be prepared as follows. Silicon wafers may be thermally oxidized to form approximately a 1 μm insulating oxide layer. A titanium/tungsten layer may be sputtered onto the oxide layer to a preferable thickness of between 100-1000 Å, followed by a layer of gold that is most preferably 800 Å thick. Next, a photoresist may be spun onto the wafer and may be dried and baked appropriately. The surface may then be exposed using a contact mask, such as a mask corresponding to that illustrated in FIG. 3. The latent image may be developed, and the wafer may be exposed to a gold-etchant. The patterned gold layer may be coated with the photodefinable polyimide, suitably baked, exposed using a contact mask, developed, cleaned in an $O_2$ plasma, and preferably imidized at 350° C. for 5 hours. An optional metallization of a backside of the wafer may be performed to act as a resistive heating element, where the immunosensor is to be used in a thermostatted format. The surface may then be printed with antibody-coated microparticles (e.g., the biolayer). Droplets, preferably of about 20 nL volume and containing 1% solid content in deionized water, may be deposited onto the sensor region and are dried in place by air drying. Optionally, an antibody stabilization reagent (supplied by SurModica Corp. or AET Ltd) may be overcoated onto the sensors. Drying the microparticles causes the microparticles to adhere to the surface of the sensors in a manner that prevents dissolution in either the sample or fluid containing the substrate. Advantageously, this method provides a reliable and reproducible immobilization process suitable for manufacturing sensor chips in high volume.

Each sensor may further be fabricated to comprise at least one chip that includes a conductivity sensor that is configured to monitor when a segment of the sample reaches the sensor. The time of arrival of the sample segment at the sensor can be used to detect leaks within the cartridge. For example, a delay in arrival of the sample at the sensor may indicate a leak within the cartridge. Additionally, the conductivity sensor may be configured to determine the position of the sample segment within a sensor conduit such that the sample segment may be actively controlled using an edge of the sample as a marker. For example, as the sample/air interface crosses the sensor, a precise signal may be generated that may be used as a fluid marker from which controlled fluid excursions may be executed. The sample segment may be preferentially oscillated edge-to-edge over the sensor in order to present the entire sample segment to the sensor surface. For example, a second reagent may be introduced in the sensor conduit beyond the sensor, which becomes homogenously distributed during the fluid oscillations.

Microparticle Reagents for Hook Detection

Microparticle based immunoassays typically employ a microparticle (uP) latex as a solid support for immunosorption in enzyme-linked immunosorbent assays (ELISA). The microparticles may be coated with an analyte-specific immunoglobulin (Ig) or antibody (e.g., the immobilized antibody) that recognizes and specifically binds to a target analyte. In some embodiments, the Ig-coated microparticles (uP-Ig1) are printed and irreversibly adsorbed above the primary sensor (e.g., an electrochemical sensor). A soluble conjugate (e.g., a second analyte specific antibody (Ig2) covalently attached to an enzyme, such as the signal antibody) may be mixed with the sample, and the mixture may be brought into contact with the primary sensor resulting in the formation of sandwiches above the primary sensor (e.g., uP-Ig1⇌Antigen⇌Ig2-Enz). The substrate is designed or configured such that the enzyme will act on the substrate to form an electroactive product that may generate an electrical current or potential across the primary sensor (e.g., an electrode).

In a preferred embodiment of the present invention, an "attenuated" microparticle (auP) reagent may be formed by coating a microparticle with less than full coverage of Ig (e.g., attenuated or reduced coverage) such that the attenuated microparticle reagent coverage may be only about 2% of the coverage for the microparticle reagent intended for the primary sensor, optionally from 0.5 to 20% of the coverage, from 1 to 10% of the coverage, or from 1 to 5% of the coverage of the microparticle reagent intended for the primary sensor. For example, where a specific microparticle may adsorb "X" Ig molecules per unit weight of microparticle, the auP may be obtained by adsorbing aX Ig molecules where a<1. In some embodiments, this may be done by coating the uP with a mixture of "a" units of analyte-specific Ig and (1-a) units of a co-absorbate (e.g., a non-specific Ig and/or proteins). The co-absorbate dilutes surface activity of the analyte-specific Ig on the microparticles adsorbed over the attenuated sensor. As should be understood by those of ordinary skill in the art, the relative analyte-specific Ig coating of the uP and the auP can be optimized for sensitivity in specific regions of the desired dynamic range of the immunoassay, precision of the analyte concentration, and hook detection ratio or signal level based on observation of the primary and attenuated sensor responses.

Alternatively, an attenuated uP reagent may be obtained by sequential adsorption of antibodies in amounts suitable to achieve the desired attenuated or reduced coverage. The non-specific Ig can be, for example, mouse or goat IgG. The analyte-specific Ig may also be diluted with other proteins, e.g., BSA or human serum albumin (HSA), or with any suitable co-adsorbate that serves the purpose of diluting surface activity of analyte-specific Ig on the microparticle (e.g., an exemplary anti-HSA bead preparation is described in U.S. Pat. No. 7,723,099). As should be understood by those of ordinary skill in the art, any means of achieving attenuated microparticle reagent coverage with non-Ig regions passivated to non-specific binding would afford the desired hook effect detection and broadening of the dynamic range without departing from the spirit and scope of the present invention.

In some embodiments, the analyte specific Ig bound to the uP may comprise a first affinity for the target analyte and the analyte specific Ig bound to the auP may comprise a second affinity for the target analyte. The first affinity may be different from or the same as the second affinity. For example, high affinity analyte specific Ig may be bound to the uP and low affinity analyte specific Ig may be bound to the auP. The signal from the relatively higher affinity analyte specific Ig plateaus at a higher analyte concentration, while the signal from the low affinity analyte specific Ig responds substantially linearly to the higher analyte concentration. Therefore, the signal from the relatively higher affinity analyte specific Ig can be used for low analyte concentration measurement, which assures the sensitivity of the immunoassay; while the signal from the relatively lower affinity analyte specific Ig can be used for higher analyte concentration measurement, which expands the immunoassay dynamic range.

In another embodiment, the attenuated uP reagent may be prepared by mixing two microparticle reagents in a desired target ratio, e.g., mix anti-analyte coated uP with HSA or other non-specifically modified uP in a desired target ratio.

Figure 4:
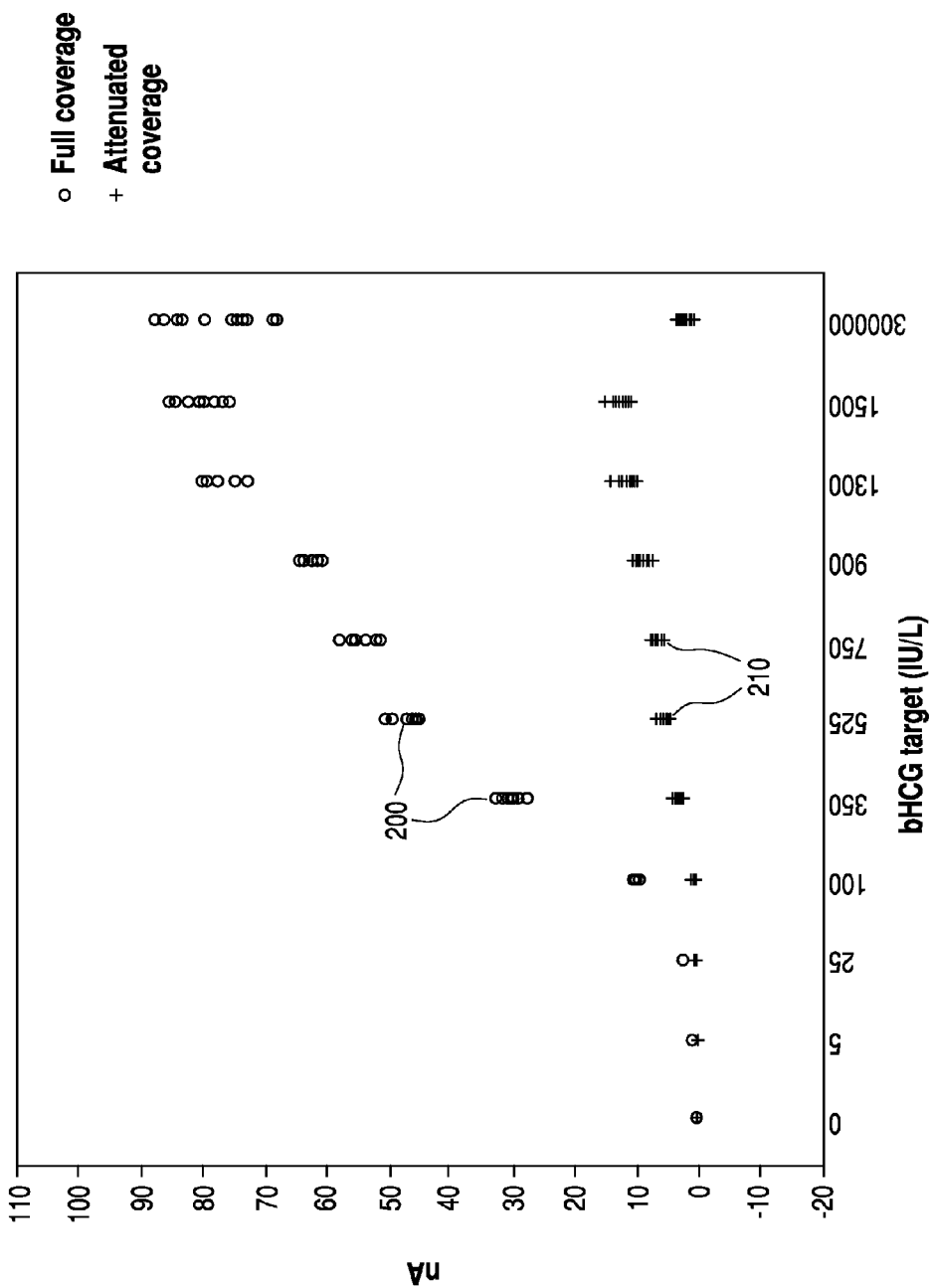
FIG. 4 illustrates the presence of the hook effect in accordance with some aspects of the invention.

FIG. 4 illustrates the signal generating properties of full-coverage Ig-uP and attenuated microparticles (auP). The recorded signals or immunosensor responses were recorded in a prototype bHCG assay as a function of analyte concentration. In particular, the open circles 200 depict the response of immunosensors printed with full-coverage Ig-uP (fcIg-uP), and the crosses 210 depict the response of immunosensors printed with attenuated coverage Ig-auP. The Ig-auP were prepared by co-adsorbing a mixture of anti-bHCG Mab and non-specific animal IgG in a mass ratio of 2:98. As can been seen in FIG. 4, the fcIg-uP response function (the open circles 200) is markedly non-linear over the range of analyte concentrations 0 to 1500 IU/L bHCG. On the other hand, the Ig-auP response function (the crosses 210) is a substantially more linear response with lower signals than the fcIg-uP response function (the open circles 200). Thus, the behavior of an Ig-auP may be sought to achieve a more linear response or achieve a lower total signal than that of a full-coverage Ig-uP.

As discussed above, the hook effect occurs when analyte concentrations are so high that all binding sites on the microparticle reagent and/or all binding sites on the enzyme-conjugate become bound with the target analyte to the extent that the formation of sandwiches comprising an enzyme label on the immobilized uP reagent is impaired. In such instances, signal generation can be markedly diminished resulting in a false negative signal. This is illustrated in FIG. 4 by the responses plotted at the highest concentration of bHCG tested, e.g., 300,000 IU/L. For example, the fcIg-uP coated sensor generated approximately the same net signal at a concentration 300,000 IU/L as at a concentration of 1500 IU/L bHCG. On the other hand, the auP coated sensor generated a signal that was effectively zero. The difference between the signals for samples at 1500 and 300,000 IU/L illustrates the utility of an attenuated sensor comprising the auP reagent. In the absence of the attenuated sensor, the result from the primary sensor at a concentration of 300,000 IU/L might incorrectly be reported in the range of approximately 1000 to 1500 IU/L. However, the attenuated sensor (e.g., hook reference sensor) provides for the result to be correctly characterized, and may be reported as ">1500 IU/L". Therefore, it is evident that tailoring the compositions of the microparticles on the sensors within a single test device, e.g., a cartridge assay, may provide the ability to both quantify a concentration of the target analyte and detect the presence of the hook effect.

Specifically, a processor of the reader device may be configured to determine the absence or lack of the hook effect when the second signal from the attenuated sensor is high (optionally above a first threshold value) and the first signal from the primary sensor is commensurately high (optionally above a second threshold value). Furthermore, the processor may be configured to determine the presence of the hook effect when the second signal from the attenuated sensor is low (optionally below a first threshold value) and the first signal from the primary sensor is high (optionally above a second threshold value). In some embodiments, the processor may determine a ratio of the first and the second signals based on relative values of the first and second signals, and determine a presence or absence of a hook effect in the immunoassay based on the determined ratio. Further, the processor may be configured to determine a concentration of the target analyte based on the presence or absence of the hook effect and the relative values of the first and second signals.

In some embodiments, at least one additional sensor may be provided comprising a biolayer having a different concentration of analyte specific Ig relative to the concentrations of the analyte specific Ig for the primary sensor and the attenuated sensor. The at least one additional sensor may be configured to generate a third signal based on the presence or absence of the target analyte in the sample. Therefore, the at least one additional sensor (e.g., N sensors, where N may be any number within some aspects of the invention) provides the ability to quantify the target analyte, detect the presence of the hook effect, and effectively broaden or increase the dynamic range of the immunoassay based on the relative values of respective first, second, and third signals.

This approach can be generalized as an array of N sensors, each of which comprises a different amount or concentration of the analyte-specific antibody and which can be engineered thusly to have a different response profile in response to different concentrations of the analyte. The response(s) from such an array of sensors when presented with a sample for analysis can be employed by a suitable algorithm to determine the concentration range in which the analyte occurs in the sample and expand the dynamic range of the immunoassay. Optionally, some of these sensors may comprise identical microparticle reagents (thus having identical dose response to analyte) allowing for improvements in precision afforded by signal averaging from like sensors (uncertainty in the mean decreases with the inverse of the square root of N).

In some embodiments, an immunosensor system is provided comprised of N immunosensors. Each of the N immunosensors may comprise different loadings or concentrations of an immobilized antibody specific to a target analyte of interest. Each immunosensor may be configured to generate a signal based on a sandwich between the immobilized antibody, the target analyte, and a labeled antibody. In this approach, the immunosensor system provides an array of N immunosensors, which have different dose-responses to the target analyte of interest, such that an immunoassay using the immunosensor system may provide quantitation of the analyte over a wider range of concentrations effectively broadening the dynamic range of the immunoassay.

Figure 5:
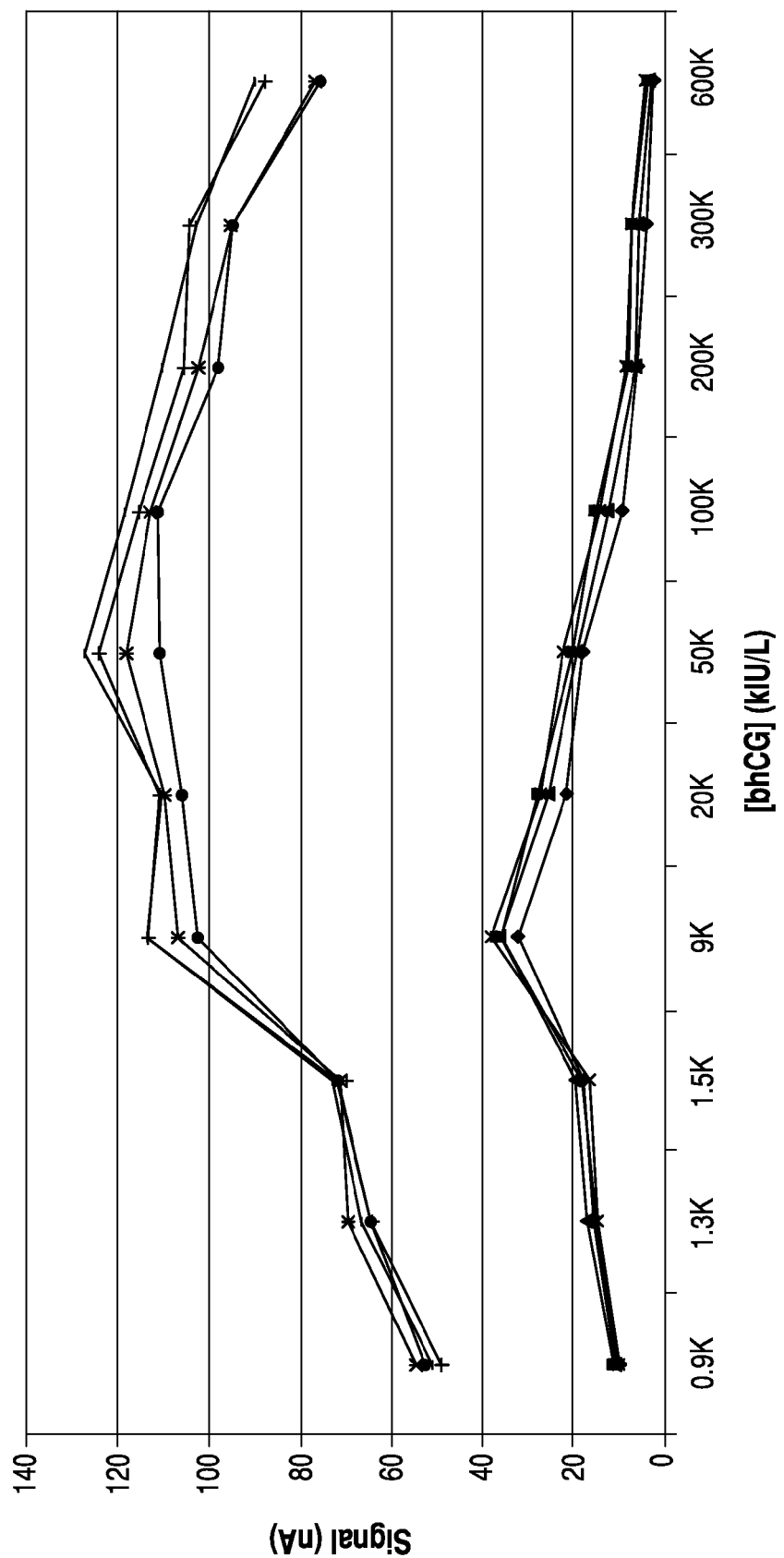
FIG. 5 illustrates extended range dose-response curves arising from assay cartridges designed to detect/quantitate beta human chorionic gonadotropin (bHCG) in accordance with some aspects of the invention.

In accordance with some aspects of the invention, cartridges may be provided for which over-range results such as those illustrated in FIG. 4 may be identified and semi-quantitated. For example, as illustrated in FIG. 5, assay cartridges may be provided that are configured to detect/quantitate bHCG over a concentration range of approximately 1000 to 600,000 IU/L; note that the x-axis in FIG. 5 is not linear. The interval for sensitive measurement of bHCG is limited to a range of zero to approximately 2000 IU/L. Thus for signals ranging from zero to approximately 70 nA on the primary sensor and from zero to approximately 20 nA on the attenuated sensor, the reader device may report a quantitative bHCG result to the user. For signals from the primary sensor greater than about 70 nA, the reader device may report ">2000 IU/mL". Alternatively, for signals exceeding 90 to 100 nA on the primary sensor, the reader device may report ">10,000 IU/L", ">50,000 IU/L", ">100,000 IU/L" and ">300,000 IU/L" for attenuated sensor signals <25 nA, <20 nA, <15 nA and <10 nA respectively. The ability to specify these ranges may depend on the precise nature of the dose response curves arising from the sensors as well as the overall imprecision with which the ensemble of manufactured devices responds to various concentrations of bHCG.

However, it should be understood to one of ordinary skill that all immunoassays are susceptible to the hook effect at a sufficiently high analyte concentrations, i.e., there will be an analyte concentration at which both sensors are subject to a hook effect to the extent that neither generates a signal that is consistent with a false negative result. Provided that the fcIguP is unaffected by a hook effect up to some point, the presence of a hook effect can be detected by means of the auP sensor. Accordingly, in some embodiments of the present invention, the primary dynamic range of such an assay (0-1500 IU/L bHCG), the loss of signal at the auP sensor may be used for quantitation or semi-quantitation of higher concentrations of bHCG.

In a preferred embodiment, the microparticle reagents for bHCG and the attenuated microparticle reagents for bHCG may be fabricated using the following process. Additionally, the microparticle reagents coated with anti-bHCG at two levels may be prepared by a similar method. The microparticles (e.g., carboxylate-modified latex microparticles (CMuP) supplied by Bangs Laboratories Inc. or Seradyn Microparticles Inc.) may be first buffer exchanged by centrifugation, followed by addition of the Ig, which is allowed to passively adsorb onto the microparticles. Carboxyl groups on the particles may be then activated with carbodiimides (EDAC) in 2-(N-morpholino)ethanesulfonic acid (MES buffer) at pH 6.2, to form amide bonds to the antibodies. Any bead aggregates may then be removed by centrifugation and the finished beads may be stored frozen in a suitable stabilizing matrix, e.g., lactitol/DEAE-dextran. In an alternative embodiment, the CMuP may be pre-activated with EDAC and subsequently reacted with the Ig. As indicated above, the coating coverage for the attenuated reagent may be only about 2% of the full coverage for the microparticle reagent intended for the primary sensor or the other ranges of coverage provided above.

In order to bind the microparticle reagents to the pair of sensors (e.g., the primary immunosensor and the attenuated immunosensor), a droplet of about 0.4 nL comprising about 1% solids (i.e., the microparticles and/or attenuated microparticles) in deionized water may be microdispensed (e.g., using the method and apparatus of U.S. Pat. No. 5,554,339, which is incorporated herein by reference in its entirety) onto a surface of the primary immunosensor and/or the attenuated immunosensor, or a photo-patterned PVA permselective layer covering the primary immunosensor and the attenuated immunosensor. The droplet may then be allowed to dry. The adherence of the dried microparticles particles to the porous layer substantially prevents dissolution of the microparticles into the sample (e.g., the blood or urine sample) or the washing fluid. However, in some embodiments additional coupling chemistry may be used to ensure bead immobilization on the porous layer and/or the immunosensors. Such techniques are well known in the art.

Additional or Alternative Systems and Reagents for Hook Detection

In a preferred embodiment of the present invention, two capture reagents may be used to detect high concentrations of a target antigen in samples that could cause the hook effect. The first reagent may comprise an antigen-binding reagent, e.g., analyte-specific Ig or antibody at a normal or "full" concentration and the second reagent may comprise the antigen-binding reagent at a substantially lower or "attenuated" concentration. In accordance with these aspects of the present invention, the amount of target antigen captured by each of these two reagents should be measured separately. In the preferred embodiment, the capture antibody may be attached to separate preparations of microparticles with one at full coating concentration and the other at an attenuated concentration as discussed herein. The microparticle may then be printed on two separate electrode sensors (e.g., a primary sensor and an attenuated sensor). The binding of the target antigen to each of these microparticles may be detected using an antibody-alkaline phosphatase conjugate. The amount of conjugate bound to the target antigen on each of the two microparticles is detected separately by measuring the current generated from the action of alkaline phosphastase by measuring this at each separate electrode.

It should be understood to those of ordinary skill in the art that the present invention can be generalized without departing from the spirit and the scope of the invention using any system that can measure separately the amount of target antigen captured by each capture reagent. In systems where the capture reagents are coated on the microparticle several methods could be used to detect the signal from each capture reagent. This could be physical as in the example above where the microparticles are printed on two different sites that can then be monitored separately. One embodiment may include printing the two different microparticles on separate spots in the bottom of a microtiter plater, a conduit of a cartridge as discussed herein, or on a nitrocellulose or other membrane. Target antigen binding to each separate spot could be detected by color formation or fluorescence detection using the labeled detection antibody. Color intensity or fluorescence could also be measured with a charge-coupled device (CCD) camera. This method could also be used if the capture antibody at two concentrations were directly spotted onto these surfaces.

In alternative embodiments, the two microparticles could be distinguished by labeling the two microparticles with different colors of fluorescent dyes. The microparticles could then be scanned for fluorescent color to indentify each separate microparticle using flow cytometry. A detection reagent with different color fluorescence could be used to detect the amount of antigen on each of the different microparticles. This system may be similar to a system used by Luminex Corp (Austin, Tex.) to distinguish microparticles coated with different antibodies and to detect the amount of antigen bound by each microparticle (see, e.g., U.S. Patent Application Publication Nos. 2012/0219457 and 2011/0206557, and U.S. Pat. No. 6,929,953, which are incorporated herein by reference in their entireties). For example, the two microparticles and sample could be introduced into an optical detection device or system, such as the Luminex system, and randomly spread in a detection chamber. The optics may be configured to image some or all of the beads and record their color and position (e.g., first primary sensor bead blue and second attenuated sensor bead green). The system may be further configured to record the florescence of each bead. Accordingly, with the positional data and algorithm could be configured to determine an average first bead fluorescence intensity (e.g., primary bead fluorescence) and an average second bead fluorescence intensity (e.g., attenuated bead fluorescence), and perform an analysis for hook detection and expansion of the dynamic range of the assay, as discussed herein with respect to the electrochemical immunosensors.

Other physical characteristics that could be used to differentiate the two types of microparticles, including but are not limited to microparticle size, microparticle color, microparticle density, presence or absence of paramagnetic properties, shape, biotin on one of two antibodies to allow separation, antibodies of two different subclasses or animal source, antibodies labeled with two different haptens to allow separation, etc.

As should be understood by those of ordinary skill in the art, although the approach of coadsorption of a mixture of proteins in which the active antibody is present in a minority is one exemplary approach to an attenuated solid phase, in principle, any means by which the density of active antibodies on the surface of a solid support can be controlled may be employed in preparing attenuated reagents suitable for application in the embodiments described herein. In preferred embodiments, it should be understood that "active" means able to associate strongly with a target ligand in solution, and thus, in additional or alternative embodiments it may be possible for a population of antibodies attached to a solid surface to be fully functional, but for reasons of orientation in which the binding domain is sterically inaccessible, are "inactive" in their ability to associate strongly with a target ligand in solution. For example, it is known to those skilled in the art that the control of reaction conditions, e.g., pH, temperature, time, antibody and/or cross-linker concentrations etc., by which an antibody is immobilized on a solid support, is important in determining the fraction of immobilized antibodies which are "active". Thus, it may be possible to generate an attenuated reagent simply by the control of reaction conditions.

In one embodiment, a pre-adsorbing a "scaffold" molecule or mixture of such molecules that act to coat the solid phase in such a way as to inhibit non-specific binding of reagents and at the same time afford "anchor" points by which a specific antibody or antibody fragment may be covalently attached may be employed. In accordance with such an embodiment, the density of the antibodies may depend on the density of anchor points achieved in the scaffold formation step.

In yet another embodiment, a solid phase may be functionalized with a controlled density of "tether" molecules to which a specific antibody or antibody fragment may then be covalently attached. In accordance with such an embodiment, the density of the tether molecules may dictate the final density of the specific antibody, antibody fragment or other receptor. If necessary to limit non-specific binding of signal generating reagents, the surface of the solid phase not covered by tether molecules may be treated with non-specific antibodies, proteins or other molecules either before or after the specific antibody or antibody fragments are covalently attached via the tether. It should be understood that although embodiments of the present invention are discussed herein with respect to analyte-specific Ig or antibody as the antigen-binding reagent, any "binding reagent" which would include any molecule capable of binding strongly to a target analyte molecule, e.g., any receptor-ligand combo, may be used without departing from the spirit and scope of the present invention.

Determination of Prostate Specific Antigen (PSA)

PSA is another example of an analyte for which the biological significant measurement range is relatively small, e.g., 0-100 ng/ml, but there is also a potential for samples with very high concentrations, e.g., 20,000 ng/ml, that may saturate the reagent and cause a hook effect. In accordance with these aspects of the present invention, a preferred embodiment may be directed to of a microfabricated sensor array where the attenuated sensor may be the same in all significant respects (e.g., dimensions, porous screening layer, latex particle coating, and metal electrode composition) as the primary sensor except that the capture or microparticle reagent for the target analyte (e.g., the biolayer comprising anti-PSA antibodies immobilized on microparticles) is present in an attenuated form, e.g., having a lower concentration of immobilized antibody relative to the immobilized antibody concentration in the primary sensor. In alternative embodiments, the two microparticles could be distinguished by labeling the two microparticles with different colors of fluorescent dyes. The microparticles could then be scanned for fluorescent color to indentify each separate microparticle using flow cytometry.

System Comprising a Sensor Array Configured for Hook Detection

Figure 6:
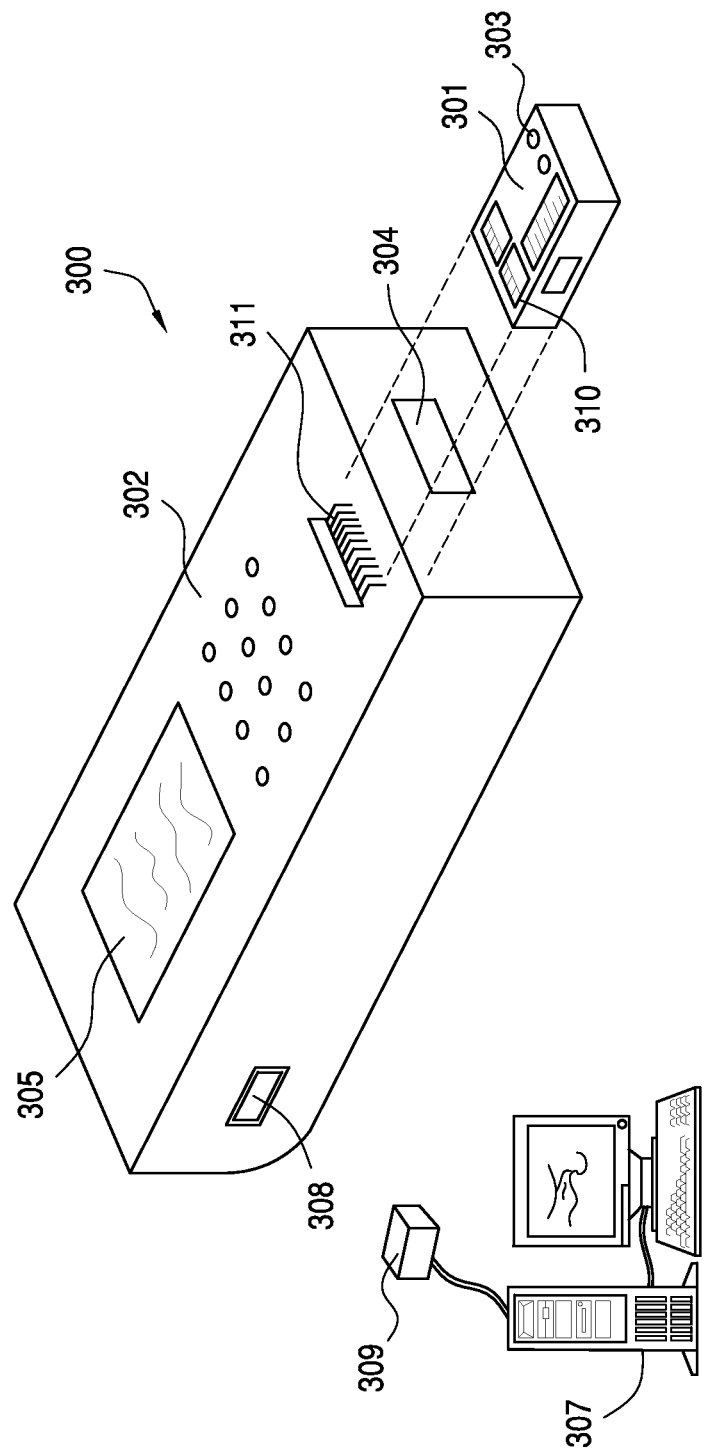
FIG. 6 shows an isometric view of a disposable sensing device and reader device in accordance with some aspects of the invention.

Referring to FIG. 6, the system 300 of the present invention may comprise a self-contained disposable sensing device or cartridge 301 and a reader device or instrument 302. A fluid sample to be measured is drawn into a sample entry orifice or port 303 in the cartridge 301, and the cartridge 301 may be inserted into the reader device 302 through a slotted opening 304. The reader device 302 may comprise a processor configured to perform measurements of analyte concentration within the fluid sample, and determine the presence or absence of the hook effect, as discussed herein in further detail. Measurements and determinations performed by the reader may be output to a display 305 or other output device, such as a printer or data management system 307 via a port on the reader 308 to a computer port 309. Transmission can be via Wifi, Bluetooth link, infrared and the like. Note that where the sensors are based on electrochemical principles of operation, the sensors 310 (e.g., the primary sensor and the attenuated sensor) in the cartridge 301 make electrical contact with the instrument 302 via an electrical connector 311. For example, the connector may be of the design disclosed in jointly owned U.S. Pat. No. 4,954,087, incorporated herein by reference in its entirety. The instrument 302 may also include a method for automatic fluid flow compensation in the cartridge 301, as disclosed in jointly owned U.S. Pat. No. 5,821,399, which also is incorporated herein by reference in its entirety.

In some aspects of the invention, the cartridge 301 may be provided with a barcode with factory set information including equations to be used and required test coefficients. The reader device 302, into which the cartridge 301 is inserted to run the test, may thus be equipped with a barcode reader. A selection of equations may be embedded in software of the reader device 302. For example, the coefficients for the cartridge 301 may differ, where different lots of cartridges 301 are manufactured, each lot having slightly different factory-determined characteristics. In any event, the coefficients for the cartridge 301, from whichever manufacturing lot the cartridge 301 is drawn, are conveyed to the reader device 302 for use in one or more of the equations, for that particular cartridge test. For example, if a given digit of the cartridge barcode is set to 1, the reader device 302 may set a predetermined coefficient to zero, whereas other digits may code for different coefficients or select a kinetic model to be used, e.g., an immunoassay model formulated by analogy to the well-known Michaelis-Menton enzyme kinetics.

Figure 9:
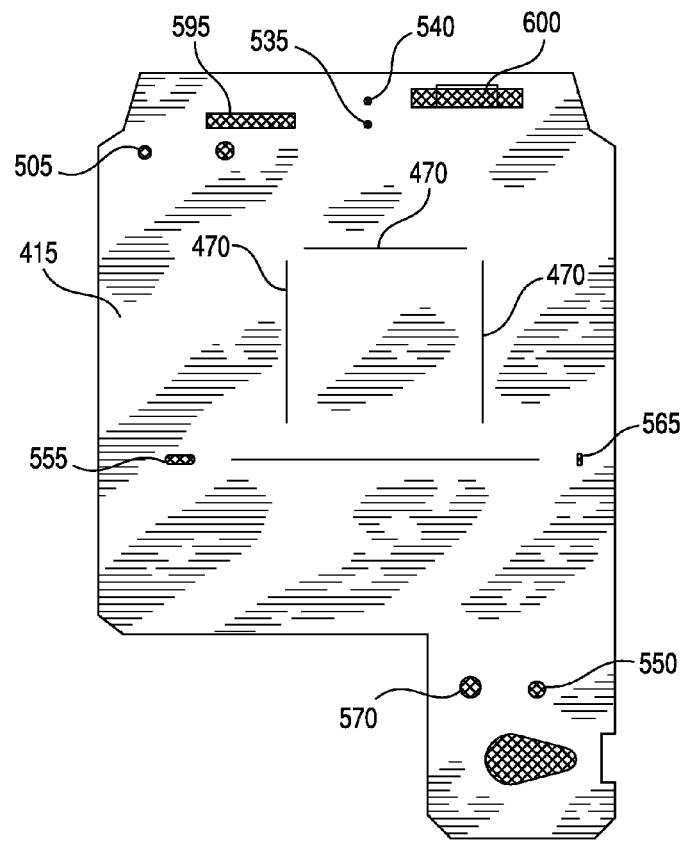
FIG. 9 shows a top view of a tape gasket in accordance with some aspects of the invention.
Figure 10:
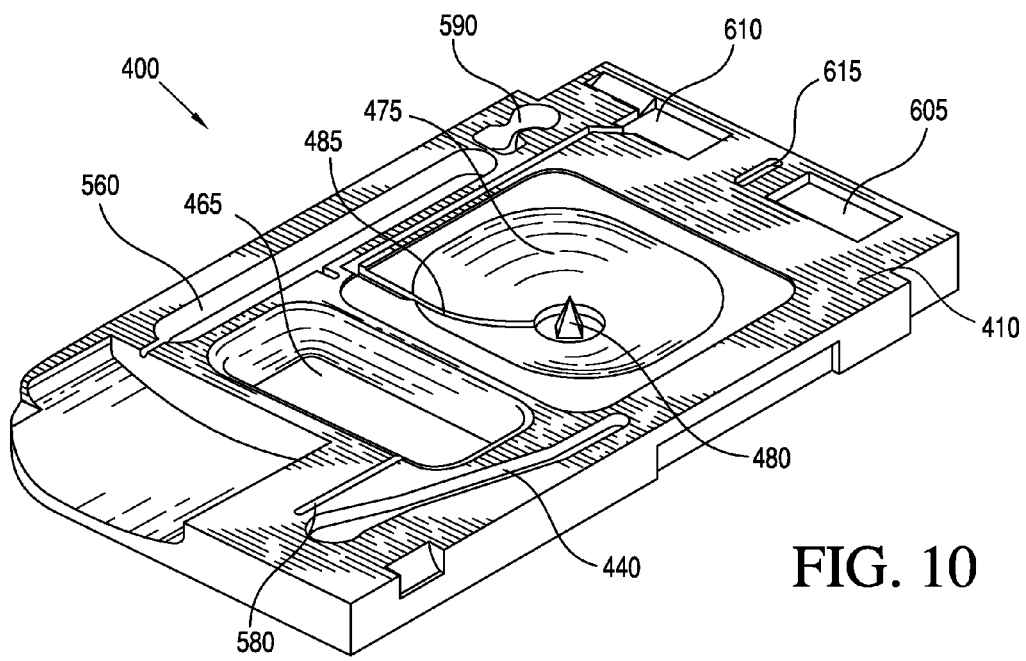
FIG. 10 shows an isometric top view of an immunosensor cartridge base in accordance with some aspects of the invention.

In one embodiment, as shown in FIGS. 7-10, a cartridge 400 (e.g., a disposable assay cartridge) may comprise a cover 405 (as shown in FIGS. 7 and 8), a base 410 (as shown in FIG. 10), and a thin-film adhesive gasket 415 (as shown in FIG. 9) that is disposed between the base 410 and the cover 405. The cartridge 400 may be configured for insertion into a reader device, and therefore the cartridge 400 may comprise a plurality of mechanical and electrical connections (not shown) for this purpose. Advantageously, a feature of the cartridge 400 is that once a sample is loaded within the cartridge 400, analysis of the sample may be completed and the cartridge 400 may discarded without an operator or others contacting the sample.

Referring to FIG. 7, the cover 405 may be made of a rigid material, preferably plastic, and capable of repetitive deformation at flexible hinge regions 420, 425, and 430 without cracking. The cover 405 may comprise a lid 435, attached to a main body of the cover 405 by the flexible hinge 425. In operation, after introduction of a sample into a sample holding chamber 440 (as shown in FIG. 10) through a sample entry port 445, the lid 435 may be secured over an entrance to the sample entry port 445, preventing sample leakage. The lid 435 may be held in place by a hook 450.

The cartridge 400 optionally may also have a closure feature as described in jointly owned U.S. Pat. No. 7,682,833, which is hereby incorporated by reference in its entirety, for sealing the sample entry port 445 in an air-tight manner. This closure device may be slidable with respect to a body of the cartridge 400 and provides a shearing action that displaces excess sample located in the region of the sample entry port 445, reliably sealing a portion of the sample in the sample holding chamber 440 between the sample entry port 445 and a capillary stop. Specifically, the cartridge 400 may be sealed by slidably moving a sealing element over the surface of the cartridge in a manner that displaces excess fluid sample away from the sample entry port 445, seals a volume of the fluid sample within the internal fluid sample holding chamber 440, and inhibits fluid sample from prematurely breaking through the internal capillary stop.

The cover 405 may further comprise two paddles 455 and 460 that are moveable relative to the body of the cover 405, and which are attached to the cover 405 by the flexible hinge regions 420 and 430. The paddle 460 may be configured to be operated by a pumping means such that a force is exerted upon an air bladder comprised of cavity 465 (as shown in FIG. 10) and the gasket 415. Operation of the paddle 460 displaces fluid within conduits of the cartridge 400.

The paddle 455 may be configured to be operated upon by a second pumping means such that a force is exerted upon the gasket 415, which can deform because of slits 470 cut therein (as shown in FIG. 9). Deformation of the gasket 415 may transmit pressure onto a fluid-containing foil pack filled with a fluid, e.g., approximately 130 µL of analysis/wash solution or fluid, located in cavity 475 (as shown in FIG. 10), rupturing the foil pack upon spike 480, and expelling fluid into conduit 485. The conduit 485 may be connected via a short transecting conduit in the base 410 to a conduit 490 (as shown in FIG. 8). The fluid fills a front of the conduit 485 first pushing fluid into a small opening in the gasket 415 that acts as a capillary stop.

Additional action in the cartridge 400 generated by mechanisms within the reading device applied to the cartridge 400 may be used to inject one or more air segments into the fluid at controlled positions within the conduit 490. The air segments may be used to wash a sensor surface of the sensor array and the surrounding conduit 490 with a minimum amount of fluid. For example, the cover 405 may further comprise a hole covered by a thin pliable film 495. In operation, pressure exerted upon the film 495 may expel one or more air segments into the conduit 490 through a small hole 505 in the gasket 415 (as shown in FIGS. 8 and 9).

Referring to FIG. 9, a lower surface of the cover 405 further comprises the conduit 490 and another conduit 510. The conduit 490 includes a constriction 520 that controls fluid flow by providing resistance to the flow of the fluid. Optional coatings 525 and 530, e.g., dry reagent coatings, may provide hydrophobic surfaces on the conduit 510, which together with gasket holes 535 and 540 control fluid flow between conduits 190 and 510. A recess 545 in the base may provide a pathway for air to enter and/or escape the conduit 440 through hole 550 in the gasket.

Referring to FIG. 9, the thin-film gasket 415 comprises various holes and slits to facilitate transfer of fluid and air between conduits within the base 405 and the cover 410, and to allow the gasket 415 to deform under pressure where necessary. Specifically, a hole 555 may permit fluid to flow from the conduit 490 into a waste chamber 560, a hole 565 may comprise a capillary stop between conduits 440 and 510, a hole 570 may permit air to flow between a recess 575 (as shown in FIG. 8) and a conduit 580 (as shown in FIG. 10), the hole 550 provides for air movement between the recess 545 and the conduit 440, and the hole 505 permits fluid to flow from a conduit 585 (as shown in FIG. 8) to the waste chamber 560 via optional closeable valve 590 (as shown in FIG. 10). Holes 595 and 600 permit a plurality of electrodes (e.g., the primary sensor and the attenuated sensor) that are housed within cutaways 605 and 610, respectively, to contact fluid within the conduit 490. In a specific embodiment, cutaway 610 houses a ground electrode, and/or a counter-reference electrode, and cutaway 605 houses at least one analyte sensor (e.g., the primary sensor) and the attenuated sensor, and optionally, a conductimetric sensor.

Referring to FIG. 10, the conduit 440 may be configured as a sample holding chamber that connects the sample entry port 445 to the conduit 510 in the assembled cartridge 400. The cutaway 605 may house at least one analyte sensor (e.g., the primary sensor) and the attenuated sensor, or an analyte responsive surface, together with an optional conductimetric sensor or sensors. The cutaway 610 may house a ground electrode if needed as a return current path for an electrochemical sensor, and may also house an optional conductimetric sensor. A cutaway 615 may provide a fluid path between gasket holes 535 and 540 such that fluid may pass between the conduits 490 and 510. Recess 475 houses a fluid-containing package, e.g., a rupturable pouch, in the assembled cartridge 400 that may be pierced by the spike 480 because of pressure exerted upon paddle 455 upon insertion of the cartridge 400 into the reading device. Fluid from the pierced package flows into the conduit 485. The air bladder may be comprised of the recess 465, which is sealed on its upper surface by the gasket 415. The air bladder may be one embodiment of a pump means, and may be actuated by pressure applied to the paddle 460, which displaces air in the conduit 580 and thereby displaces the sample from the sample chamber 440 into the conduit 510.

In some embodiments, a metering means may optionally comprise the sample chamber 440 bounded by the capillary stop 565 and having along the chamber 440 length an air entry point (gasket hole 550) from the bladder. Air pressure exerted at the gasket hole 550 drives a metered volume of the sample past the capillary stop 565. Therefore, a metered volume of sample may be predetermined by a volume of the sample chamber 440 between the air entry point 550 and the capillary stop 565. An amount of the sample corresponding to this volume may be displaced into the conduit 510 when the paddle 460 is displaced. This arrangement may therefore provide a metering means for delivering a metered amount of an unmetered sample into the various downstream conduits of the cartridge 400. The metering may be advantageous in some embodiments if quantitation of the analyte is required. Thus, an operator may be relieved of accurately measuring the volume of the sample prior to measurement saving time, effort, and increasing the accuracy and reproducibility.

Figure 11:
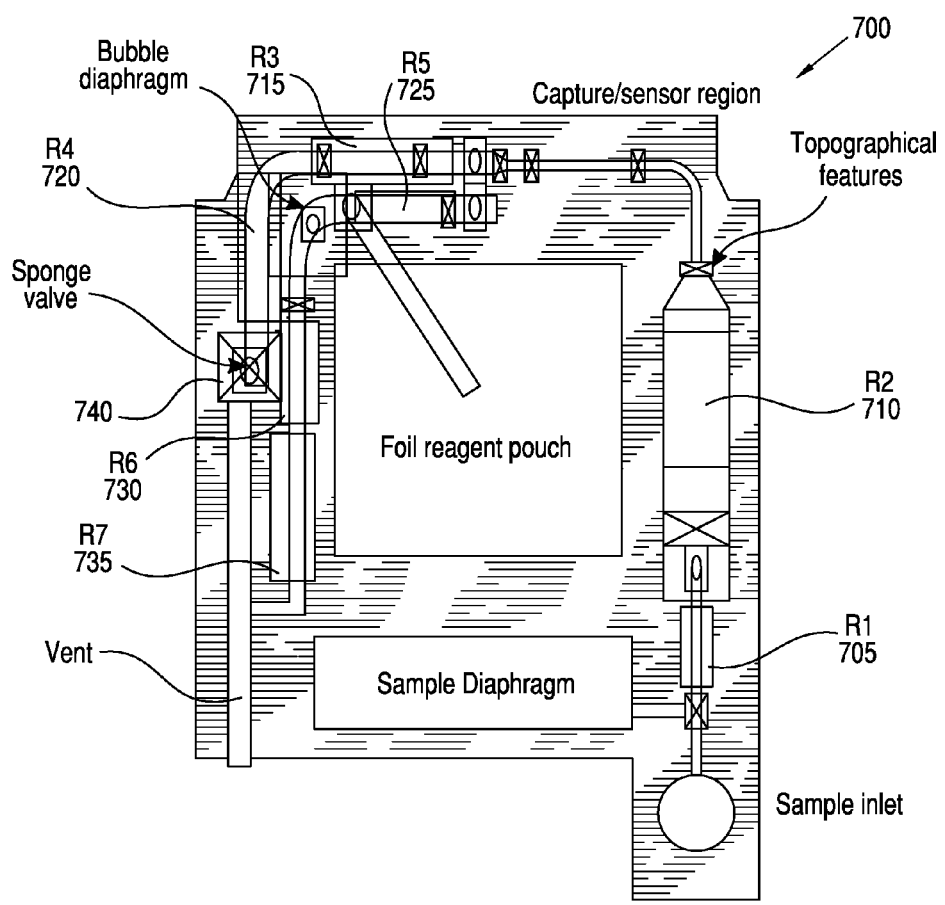
FIG. 11 shows a schematic view of the layout of an immunosensor cartridge in accordance with some aspects of the invention.

As shown in FIG. 11, a schematic diagram of the features of the cartridge 700 and components therein is provided. Specifically, in preferred embodiments, the conduits and the sample chamber 705-735 may optionally be coated with dry reagents to amend the sample or fluid. The sample or fluid may be passed at least once over the dry reagent to dissolve the dry reagent. Reagents that may be used to amend samples or fluid within the cartridge include antibody-enzyme conjugates, or blocking agents that prevent either specific or non-specific binding reactions among assay compounds. A surface coating that may not be soluble but helps prevent non-specific adsorption of assay components to the inner surfaces of the cartridge 700 may also be provided.

For example, within a segment of the sample or fluid, an amending substance may be preferentially dissolved and concentrated within a predetermined region of the segment. In one embodiment, this may be achieved through control of the position and movement of the segment within the conduits and the sample chamber 705-735. Therefore, if only a portion of a segment, such as the leading edge, is reciprocated over the amended substance, then a high local concentration of the substance can be achieved close to the leading edge. Alternatively, if a homogenous distribution of the substance is desired, for example if a known concentration of an amending substance is required for a quantitative analysis, then further reciprocation of the sample or fluid may result in mixing and an even distribution.

In preferred embodiments, a closeable valve 740 may be provided between a first conduit and the waste chamber. In one embodiment, the valve 740 may be comprised of a dried sponge material that is coated with an impermeable substance. In operation, contacting the sponge material with the sample or a fluid may result in swelling of the sponge to fill the cavity (e.g., the valve 590 cavity as shown in FIG. 10), thereby substantially blocking further flow of liquid into the waste chamber. Furthermore, the wetted valve 740 may also be configured to block the flow of air between the first conduit and the waste chamber, which permits a first pump means connected to the sample chamber to displace fluid within a second conduit, and to displace fluid from the second conduit into the first conduit in the following manner.

After the sample is exposed to the sensor array (e.g., the primary sensor and the attenuated sensor) for a controlled time, the sample may be moved into a post-analytical conduit where the sample may be amended with another reagent. The sample may then be moved back to the sensor array and a second reaction period may begin. Alternately, the post-analysis conduit may serve simply to separate the sample segment from the sensor array. Within the post-analysis conduit may be a single closeable valve that connects an air vent of the sensor conduit to a diaphragm air pump. When the single closeable valve closes, the sample may be locked in the post analytical conduit and cannot be moved back to the sensor array.

There may be several different design examples for the single closeable valve that are encompassed within the present invention. Some designs are may be activated mechanically while others may be activate based on liquid contact. Other types of closeable valve that may be encompassed by the present invention include, but are not limited to: a flexible flap held in an open position by a soluble glue or a gelling polymer that dissolves or swells upon contact with a fluid or sample thus causing the flap to close; and alternatively, in one specific embodiment, a thin layer of a porous paper or similar material interposed between a conduit and either the waste chamber or ambient air such that the paper is permeable to air while dry but impermeable when wet. In the latter case, it may not be necessary that the closeable valve be interposed between a conduit and the waste chamber. The valve passes little to no liquid before closing and so the valve is appropriately placed when positioned between a conduit and the ambient air surrounding the cartridge. In practical construction, a piece of filter paper is placed on an opening in the tape gasket in the fluid path to be controlled. Air can readily move through this media to allow fluid to be moved through the fluid path. When the fluid is pushed over this filter, the filter media becomes filled with liquid and further motion through the fluid path is stopped. Once the filter becomes wet, significant pressures would be required to move liquid through the pores of the filter. Airflow through the filter may also be prevented because of the higher pressure required to push the liquid out of the filter, typically termed bubble pressure. This valve embodiment requires very little liquid to actuate the valve, and actuation occurs rapidly and reliably. Materials, their dimensions, porosity, wettability, swelling characteristics and related parameters are selected to provide for rapid closure, within one second or more slowly, e.g., up to 60 seconds, after first contacting the sample, depending on the specific desired closure time.

Alternatively, the closeable valve may be a mechanical valve. In this embodiment, a latex diaphragm may be placed in the bottom of the air bladder on top of a specially constructed well. The well contains two openings that fluidically connect the air vent to the sample conduit. As the analyzer plunger pushes to the bottom of the air bladder, the plunger presses on this latex diaphragm, which is adhesive backed, and seals a connection between the two holes. This connection blocks the sample's air vent, locking the sample in place.

Figure 12:
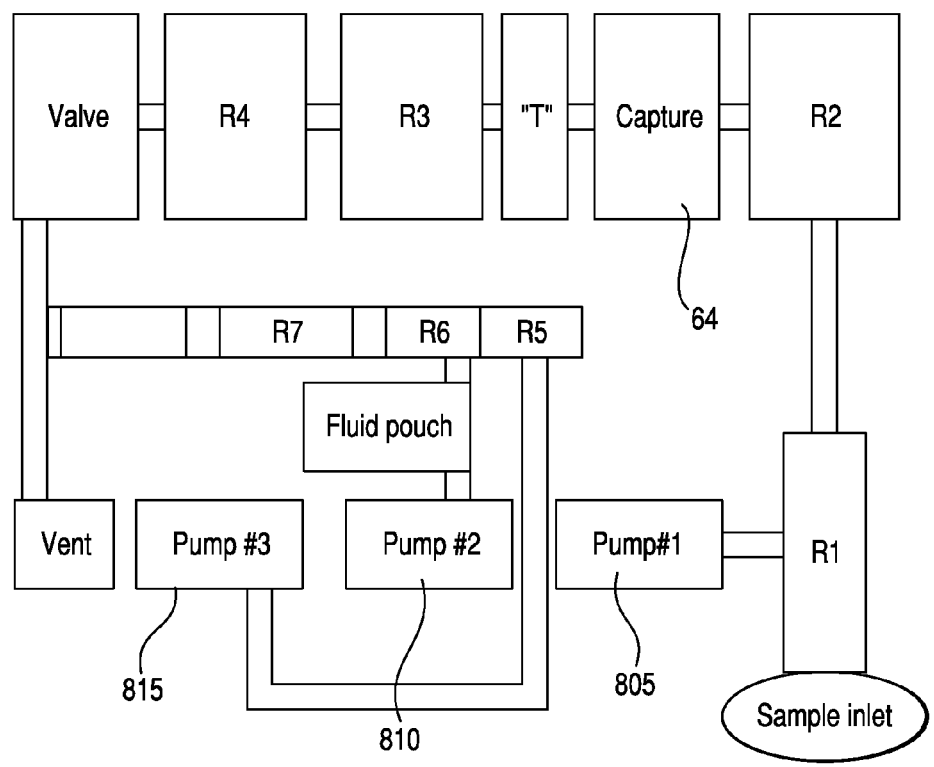
FIG. 12 shows a schematic view of the fluid and air paths within an immunosensor cartridge in accordance with some aspects of the invention.

As shown in FIG. 12, the cartridge 700 may be provided with three pump means 805-815. While these pumps are described in terms of specific embodiments, it may be readily understood that any pump means capable of performing the respective functions of the pump means 805-815 may be used within the present invention. Specifically, pump means 1, 805 should be capable of displacing the sample from the sample holding chamber into the first conduit; pump means 2, 810, should be capable of displacing fluid within the second conduit; and pump means 3, 815, should be capable of inserting at least one segment into the second conduit. Other types of pump which are envisaged in the present application include, but are not limited to, an air sac contacting a pneumatic means whereby pressure is applied to said air sac, a flexible diaphragm, a piston and cylinder, an electrodynamic pump, and a sonic pump. With reference to pump means 3, 815, the term "pump means" includes all methods by which one or more segments are inserted into the second conduit, such as a pneumatic means for displacing air from an air sac, a dry chemical that produces a gas when dissolved, or a plurality of electrolysis electrodes operably connected to a current source. In a specific embodiment, the segment may be produced using a mechanical segment generating diaphragm that may have more than one air bladder or chamber. The well 495 (as described with respect to FIG. 7) may have a single opening that connects the inner diaphragm pump and the fluid filled conduit into which a segment is to be injected. The diaphragm may be segmented to produce multiple segments, each injected in a specific location within a fluid filled conduit.

In some embodiments, a segment may be injected using a passive feature. A well in the base of the cartridge may be sealed by tape gasket. The tape gasket covering the well may have two small holes on either end. One hole may be open while the other hole may be covered with a filter material that wets upon contact with a fluid. The well may be filled with a loose hydrophilic material such as a cellulose fiber filter, paper filter or glass fiber filter. This hydrophilic material draws the liquid into the well in the base via capillary action, displacing the air, which was formerly in the well. The air is expelled through the opening in the tape gasket creating a segment whose volume is determined by the volume of the well and the void volume of the loose hydrophilic material. The filter used to cover one of the inlets to the well in the base may be chosen to meter the rate at which the fluid fills the well and thereby control the rate at which the segment is injected into the conduit in the cover. This passive feature may permit any number of controlled segments to be injected at specific locations within a fluid path and may require a minimum amount of space.

In a preferred embodiment of the present invention, the sample and a fluid, e.g., a combined wash and enzyme substrate delivery fluid, may contact the sensor array (e.g., the primary sensor and the attenuated sensor) at different times during an assay sequence. The sample and the fluid may also be independently amended with other reagents or compounds present initially as dry coatings within respective conduits of a test device, e.g., the cartridge. Controlled motion of the fluid by the above-described pumping means within the cartridge further permits more than one substance to be amended into each fluid whenever the sample or the fluid is moved to a new region of the conduit. In this manner, multiple amendments to each fluid may be accommodated, extending the complexity of automated assays that can be performed in the cartridge. Therefore, the utility of the present invention may be enhanced.

In an alternative embodiment, as shown in FIGS. 13A-13E, the cartridge 900 may include a housing that comprises two complimentary halves of a cartridge (e.g., the cover 901 and the base 902), which can be bonded together to abut and attach the two complimentary interior surfaces of the two halves in a closed position. In some embodiments, the cover 901 and the base 902 are preferably injection molded, for example, by machine as disclosed in U.S. patent application Ser. No. 13/530,501, filed on Jun. 22, 2012, which is incorporated herein by reference in its entirety. Preferably, the cover 901 is injection molded where a first substantially rigid zone 920 is formed in a first injection molding step and a substantially flexible zone 922 is formed in an additional injection molding step. Preferably, the base 902 is injection molded where a second substantially rigid zone 924 is formed in a first injection molding step. While the above-described embodiment has been described comprising a cover formed using a two-shot molding process and a base formed using a one-shot molding process, it should be understood that the cover could be formed using a one-shot molding process and the base formed using a two shot molding process, or both the cover and the base could be formed using a two-shot molding process depending on where the substantially rigid zone and the substantially flexible zones are to be located within the housing of the cartridge.

As shown in FIGS. 13A-13E, the substantially rigid zones 920 and 924 of the cover 901 and the base 902 respectively are preferably each a single contiguous zone; however, the molding process can provide a plurality of non-contiguous substantially rigid zones. The substantially flexible zone 922 is preferably a set of several non-contiguous zones. For example, the substantially flexible zone 922 around a displaceable membrane 925 may be separate and distinct from the substantially flexible zone at a closeable sealing member 928. Alternatively, the substantially flexible zone may comprise a single contiguous zone.

In a preferred embodiment, the cartridge housing comprises a sensor recess 930 in a portion of the substantially flexible zone. An advantage is that the sensors 935 (e.g., the primary sensor and the attenuated sensor preferably each of a size of about 0.3×0.4 cm), which are disposed in the sensor recess 930 preferably are made on a silicon wafer substrate, which is relatively brittle. Thus, providing a substantially flexible sensor recess 930 results in a suitable support that can protect the sensor from cracking during assembly. Note that other non-silicon based sensors may be used, e.g., those made on a plastic substrate; however, the preferred embodiment uses sensors of the type described in U.S. Pat. Nos. 5,200,051, 5,514,253, and 6,030,827, the entireties of which are incorporated herein by reference. In addition to being substantially flexible, sensor recess 930 may be best selected to form a liquid-tight and/or air-tight seal around the sensor perimeter, thereby ensuring that liquids do not leak out of the conduit that covers the sensor in the fully assembled cartridge. In an alternative embodiment, sensor recess 930 can be formed in a portion of the substantially rigid zone (as shown in FIG. 10) of either or both of the cover or the bottom of the housing. In this aspect, a liquid-tight and/or air-tight seal optionally may be formed by the double-sided adhesive sheet 415 or gasket (as shown in FIG. 9).

With regard to overall dimensions, the preferred embodiment of the molded parts shown in FIGS. 13A-13E include the cover 901 with dimensions of about 6.0 cm×3.0 cm×0.2 mm and the base 902 with dimensions of about 5.0 cm×3.0 cm×0.2 mm to provide a cartridge 900 with dimensions of about 6.0 cm×3.0 cm×0.4 cm. In terms of ranges, the cartridge 900 optionally has a length of from 1 to 50 cm, e.g., from 5 to 15 cm, a width of from 0.5 to 15 cm, e.g., from 1 to 6 cm, and a thickness of from 0.1 to 2 cm, e.g., from 0.1 to 1 cm.

Processes for Hook Detection

In preferred embodiments, a process for using a cartridge to determine the hook effect is provided. The process may include introducing an unmetered fluid sample into the sample chamber 440 of the cartridge 400 through the sample entry port 445 (as shown in FIGS. 7-10). Capillary stop 565 prevents passage of the sample into conduit 510 at this stage, and conduit 440 is filled with the sample. Lid 435 is closed to prevent leakage of the sample from the cartridge. The cartridge may then be inserted into the reading device or apparatus 302, as shown in FIG. 6 and further disclosed in U.S. Pat. No. 5,821,399, which is hereby incorporated by reference. Insertion of the cartridge into the reading apparatus activates a mechanism, which punctures the fluid-containing package located at recess 475 when the package is pressed against spike 480. Fluid is thereby expelled into the conduits 485 and 490, arriving in sequence at the sensor region. The constriction 520 prevents further movement of fluid because residual hydrostatic pressure is dissipated by the flow of fluid via the conduit 585 into the waste chamber 560.

In a second step, operation of a pump means applies pressure to the air-bladder comprised of cavity 465, forcing air through the conduit 580 and into conduit 440 at a predetermined location. Capillary stop 565 delimits a metered portion of the original sample. While the sample is within sample chamber 440, it is optionally amended with a compound or compounds present initially as a dry coating on the inner surface of the chamber, e.g., antibodies to bHCG labeled with ALP. The metered portion of the sample is then expelled through the capillary stop 565 by air pressure produced within air bladder comprised of cavity 465. The sample passes into the sensor conduit and into contact with the primary sensor and the attenuated sensor located within the cutaway 605.

To promote binding of the analyte, e.g., bHCG to the primary sensor and the attenuated sensor, the sample containing the analyte may optionally be passed repeatedly over the two sensors in an oscillatory motion. Preferably, an oscillation frequency of between about 0.2 and 2 Hz is used, most preferably 0.7 Hz. After a period, e.g., 10 minutes, for the analyte/enzyme-antibody conjugate complex to bind to the immunosensors, the sample may be ejected by further pressure applied to the air bladder comprised of cavity 465, and the sample passes to waste chamber 560. A wash step next removes non-specifically bound enzyme-conjugate from the sensor chamber. Fluid in the conduct 490 may be moved by a pump means, into contact with the sensors. The analysis fluid may be pulled slowly until a first air segment is detected at a conductivity sensor, as described herein. Note that it may be an object of the invention that the rinsing is not sufficiently protracted or vigorous as to promote dissociation of specifically bound analyte or analyte/antibody-enzyme conjugate complex from the sensors.

Use of a cartridge with a closeable valve, preferably located between the sensor chamber and the waste chamber, is herein illustrated by a specific embodiment in which the concentration of bHCG is determined within a blood sample, which is introduced into the sample chamber of said cartridge. In the following time sequence, time zero (t=0) represents the time at which the cartridge is inserted into the cartridge reading device. Times are given in minutes. Between t=0 and t=1.5, the cartridge reading device makes electrical contact with the sensors through pads 170, 175, 180, and 185 (as shown in FIG. 3), and performs certain diagnostic tests. Insertion of the cartridge perforates the foil pouch introducing fluid into a conduit as previously described. The diagnostic tests determine whether fluid or sample is present in the conduits using the conductivity electrodes; determine whether electrical short circuits are present in the electrodes; and ensure that the sensor and ground electrodes are thermally equilibrated to, preferably, 37° C. prior to the analyte determination.

Various options exist for managing any temperature effect on an immunoassay of this type. For example, the assay can be run in a system where the sample and other fluids and reagents are thermostated at a given temperature, e.g., 37° C. Alternatively, the assay may be run at ambient temperature, without any correction, or with correction to a standardized temperature based on measurement of the ambient value Between t=1.5 and t=6.75, a metered portion of the sample, preferably between 4 and 200 uL, more preferably between 4 and 20 uL, and most preferably 7 uL, may be used to contact the sensors as described above. The edges defining the forward and trailing edges of the sample are reciprocally moved over the sensor region at a frequency that is preferably between 0.2 to 2.0 Hz, and is most preferably 0.7 Hz. During this time, the enzyme-antibody conjugate dissolves within the sample, as previously described. The amount of enzyme-antibody conjugate that is coated onto the conduit is selected to yield a concentration when dissolved that is preferably higher than the highest anticipated HCG concentration, and is most preferably six times higher than the highest anticipated HCG concentration in the sample.

Between t=6.75 and t=10.0 the sample may be moved into the waste chamber via the closeable valve, wetting the closeable valve and causing it to close as previously described. The seal created by the closing of the valve permits the first pump means to be used to control motion of fluid from the sensor conduit to the post analysis conduit. After the valve closes and any remaining sample is locked in the post analysis conduit, the analyzer plunger retracts from the flexible diaphragm of the pump means creating a partial vacuum in the sensor conduit. This forces the analysis fluid through the small hole in the tape gasket and into a short transecting conduit in the base. The analysis fluid is then pulled further and the front edge of the analysis fluid is oscillated across the surface of the sensor chip in order to shear the sample near the walls of the conduit. A conductivity sensor on the sensor chip may be used to control this process. The efficiency of the process may be monitored using the amperometric sensors through the removal of unbound enzyme-antibody conjugate which enhances the oxidation current measured at the electrode when the enzyme substrate, p-aminophenyl phosphate is also present. The amperometric electrodes may be polarized to 0.06 V versus the silver chloride reference-ground electrode. In this embodiment, the fluid may be composed of a 0.1 M carbonate or diethanolamine buffer, at pH 9.8, with 1 mM $MgCl_2$, 1.0 M NaCl, 10 mM p-aminophenylphosphate, and 10 .mµ.M NaI. The efficiency of the wash is optimally further enhanced by introduction into the fluid of one or more segments that segment the fluid within the conduit as previously described. Following removal of wash fluid from the sensor channel leaving a thin layer of fluid over the two sensors, measurement of each sensor response is recorded and the concentration of analyte determined as described above and checked for the presence of the hook effect in the assay

EXAMPLES

For purposes of illustration and not limitation, the following examples provide information on the hook effect and some aspects of the present invention including the attenuated sensor configured to detect the presence of the hook effect.

Figure 14:
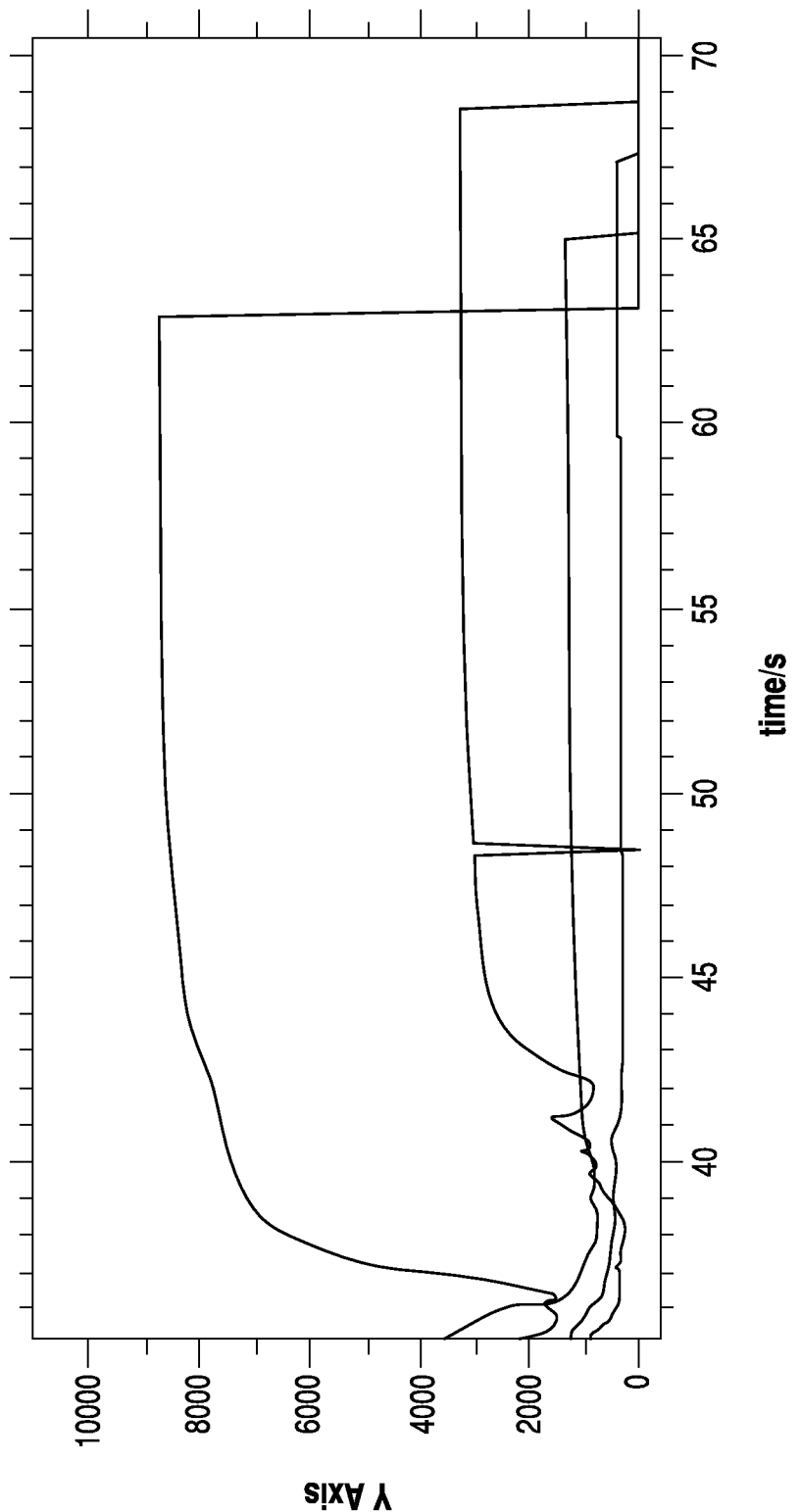
FIG. 14 shows dose-response results obtained using HCG and an HCG-responsive amperometric immunosensor in accordance with some aspects of the invention.
Figure 15:
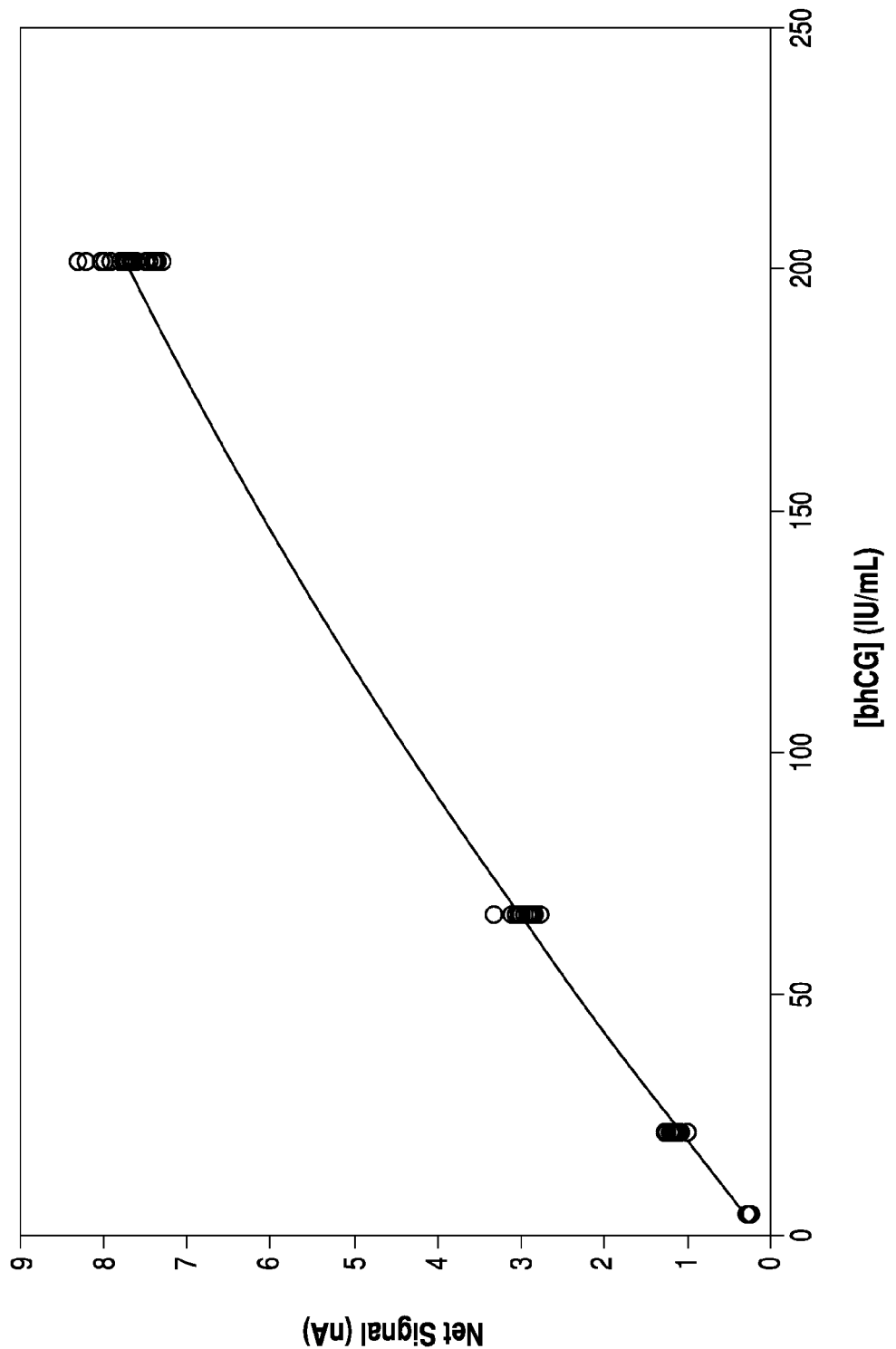
FIG. 15 shows good sensitivity of the response of the HCG-responsive amperometric immunosensor to increasing HCG in accordance with some aspects of the invention.

Dose-response results (e.g., raw immunosensor currents) obtained using human chorionic gonadotropin (hCG) and an hCG-responsive amperometric immunosensor are shown in FIG. 14. Amounts of hCG equivalent to 0 to 200 miU/mL were allowed to bind to the immobilized antibody attached to the electrode, as in FIG. 4. As shown in FIG. 15, good sensitivity of the response of the attenuated sensor to increasing hCG was found. Consequently, it was demonstrated that preferred embodiments of the present invention may precisely and rapidly quantify hCG in a sample.

With regard to handling more subtle differences between the pair of sensors, e.g., where there is a characteristic constant offset between the pair of sensors, the offset can be subtracted. Therefore, it may be recognized that it may not be necessary for the attenuated sensor to have all the same properties as the primary immunosensor, only that the attenuated immunosensor be consistently proportional in both the wash and non-specific binding parts of the assay. An algorithm embedded in the analyzer may be configured to account for any other essentially constant difference between the pair of sensors.

As discussed above with respect to hook detection, a preferred embodiment is described with reference to a bHCG cartridge cycle, which involves amperometric measurements with a pair of immunosensors. The first bHCG immunosensor (e.g., the primary immunosensor), comprises the immunoassay reagent capable of specific binding of bHCG to the sensor surface, and the second bHCG immunosensor (e.g., the attenuated immunosensor) comprises the attenuated immunoassay reagent capable of specific binding bHCG to the sensor surface.

Figure 16:
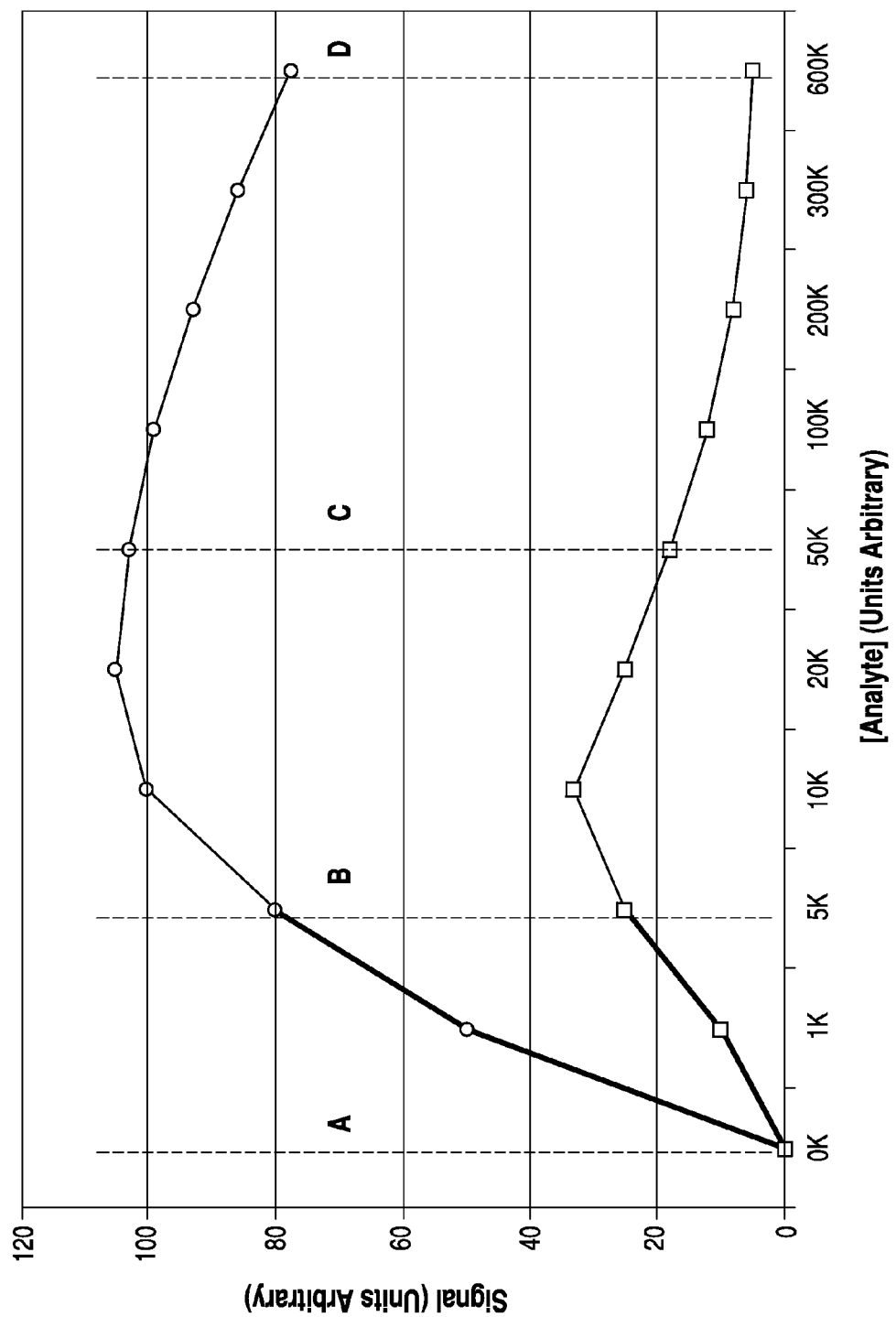
FIG. 16 illustrates conceptual concentration dose-responses from a dual sensor arrangement for an arbitrary analyte assayed over a wide concentration range in accordance with some aspects of the invention.

FIG. 16 illustrates a conceptual concentration dose-responses from such a dual sensor arrangement for an arbitrary analyte assayed over a wide concentration range, e.g., 0-600,000 units. These are qualitatively similar to theoretical curves found in FIG. 2 of Fernando, S. et al., "Studies of the 'hook' effect in the one-step sandwich immunoassay", Journal of Immunological Methods, 1992, pp. 47-66 ("Fernando and Wilson"). If confined to a single sensor, e.g., a standard immunosensor, shown as open circular points, one can see that the response at 5K analyte units is indistinguishable from that at 600K units. Therefore, the assay is said to "hook" at 600K because the signal at this level drops to that within the dynamic range of the sensor, i.e., the signal range for 0-5K analyte units indicated by the bold solid line. Similarly, if confined to a single sensor, e.g., the attenuated sensor, shown as open square points, the response at 5K is indistinguishable from that at 20K analyte units. However, if one considers the response of both sensors simultaneously, these ambiguities are resolved because the low capacity sensor (auP) response diminishes more rapidly at higher analyte concentrations than does the uP sensor. When both sensors exhibit signals approaching zero (A in FIG. 16), a zero-analyte concentration is indicated and the instrument used to read the signals would report a quantitative result to the user. When the sensors exhibit signals near the high end of the dynamic range (B in FIG. 16), a concentration near 5000 units is indicated and the instrument would report a quantitative result.

In contrast, if the sensors exhibited signals inconsistent with expectations within the dynamic range, e.g. C and D in FIG. 16), the instrument would report an over-range result, e.g. ">5000 units". Alternatively, depending on the degree of incongruence of the dose-response curves and the precision associated with measurements at each sensor, it may be feasible to report for C and D, 50,000 units and 600,000 units respectively, or semi-quantitative results of >20,000 units and >300,000 units respectively. The degree to which over-range results can be quantitated may depend on a lack of congruence between the two dose-responses (uP and auP) and the precision associated with the signal measurement over the entire range of analyte concentrations.

Of interest is the relative binding capacities of the two sensors and the effect of these binding capacities on the forms of their respective dose-response curves. Of particular interest is the degree to which the curves are not congruent (non-superimposable even with application of a scaling factor), for it is the lack of congruence that underpins the ability to identify different concentration regimes by comparing the signals from the two sensors. In their theoretical treatment, Fernando and Wilson demonstrated that as the binding capacity of the solid phase [capture] reagent increases, the range of concentrations over which the analyte can be measured with precision and the concentrations beyond which the signal begins to diminish due to the hook effect, also increase. Thus one may expect that the greatest incongruities in dose response may be achieved by reducing the binding capacity of the secondary [auP hook] sensor as much as practically possible, i.e., and still allowing measurement of meaningful, analyte-dependent signal at both sensors.

In practice, this may be achieved at binding capacities less than 5% of maximal or less than 5% of the primary sensor binding capacity. The optimal formulation may also be dependent on the dynamic range of the assay (range of quantitation) and the potential range of concentration of the analyte, e.g. one need only measure in the range from 0 to 2000 IU/L bHCG to detect pregnancy or ectopic pregnancy but bHCG may approach 300,000 IU/L at later stages of gestation or several million IU/L in the presence of certain cancers. In practical applications, optimal binding capacities are likely best determined through empirical means.

Figure 17:
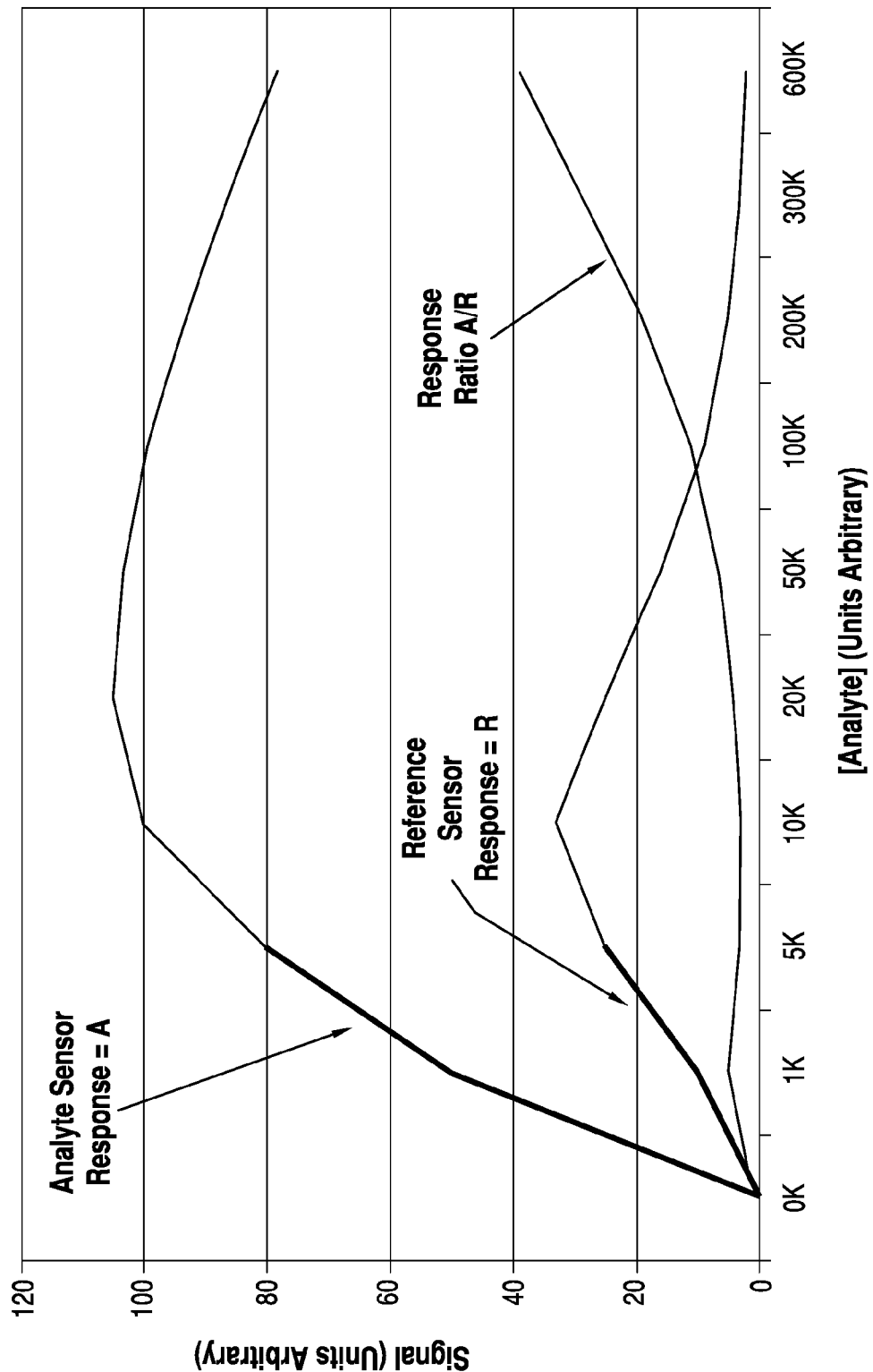
FIG. 17 illustrates the use of a sensor response ratio as a means for detecting a hook effect and expanding a dynamic range of an assay in accordance with some aspects of the invention.
Figure 18:
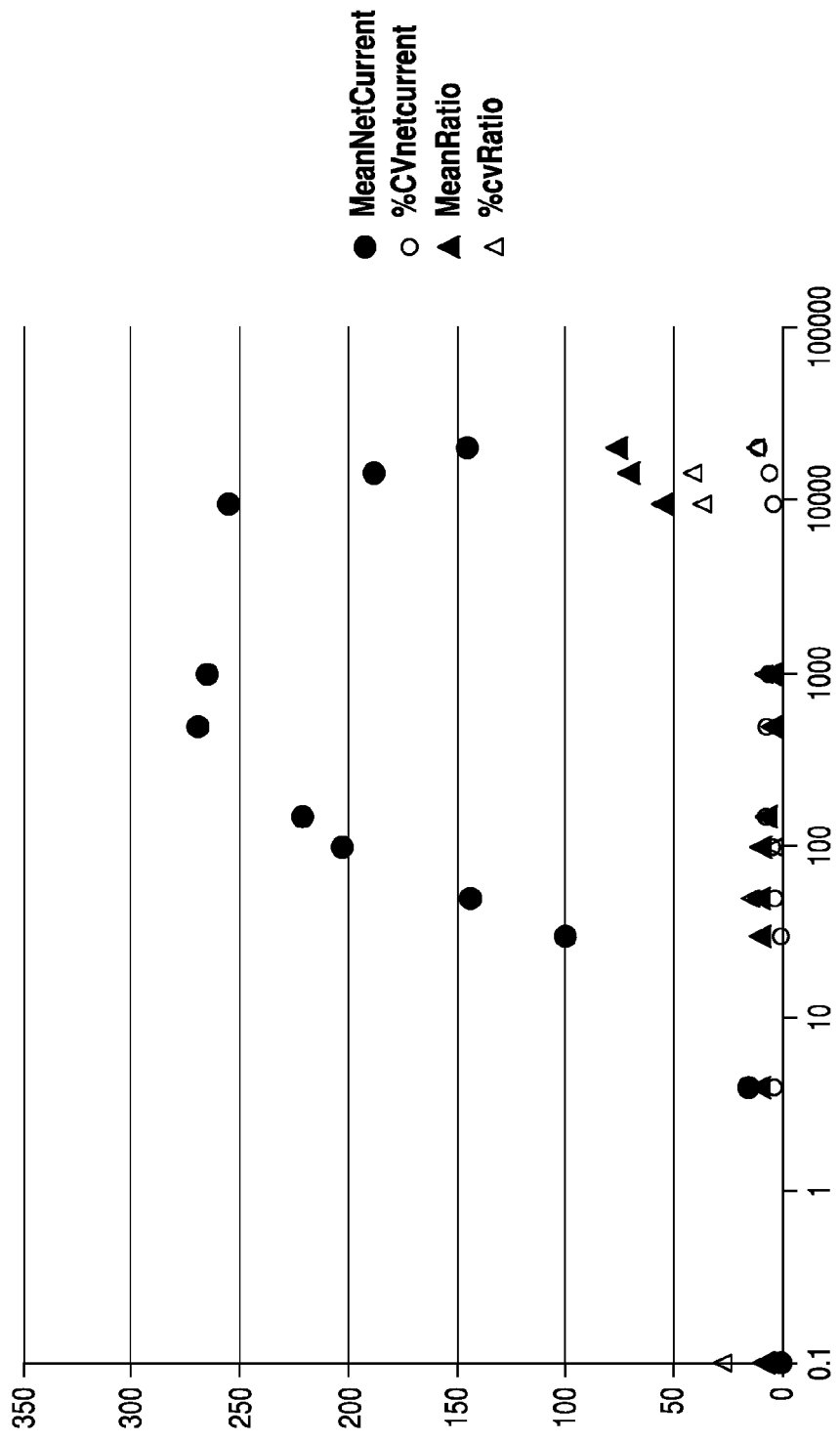
FIGS. 18, 19, and 20 illustrate data for prostate specific antigen assays using three different "attenuated" reference reagents in accordance with some aspects of the invention.
Figure 19:
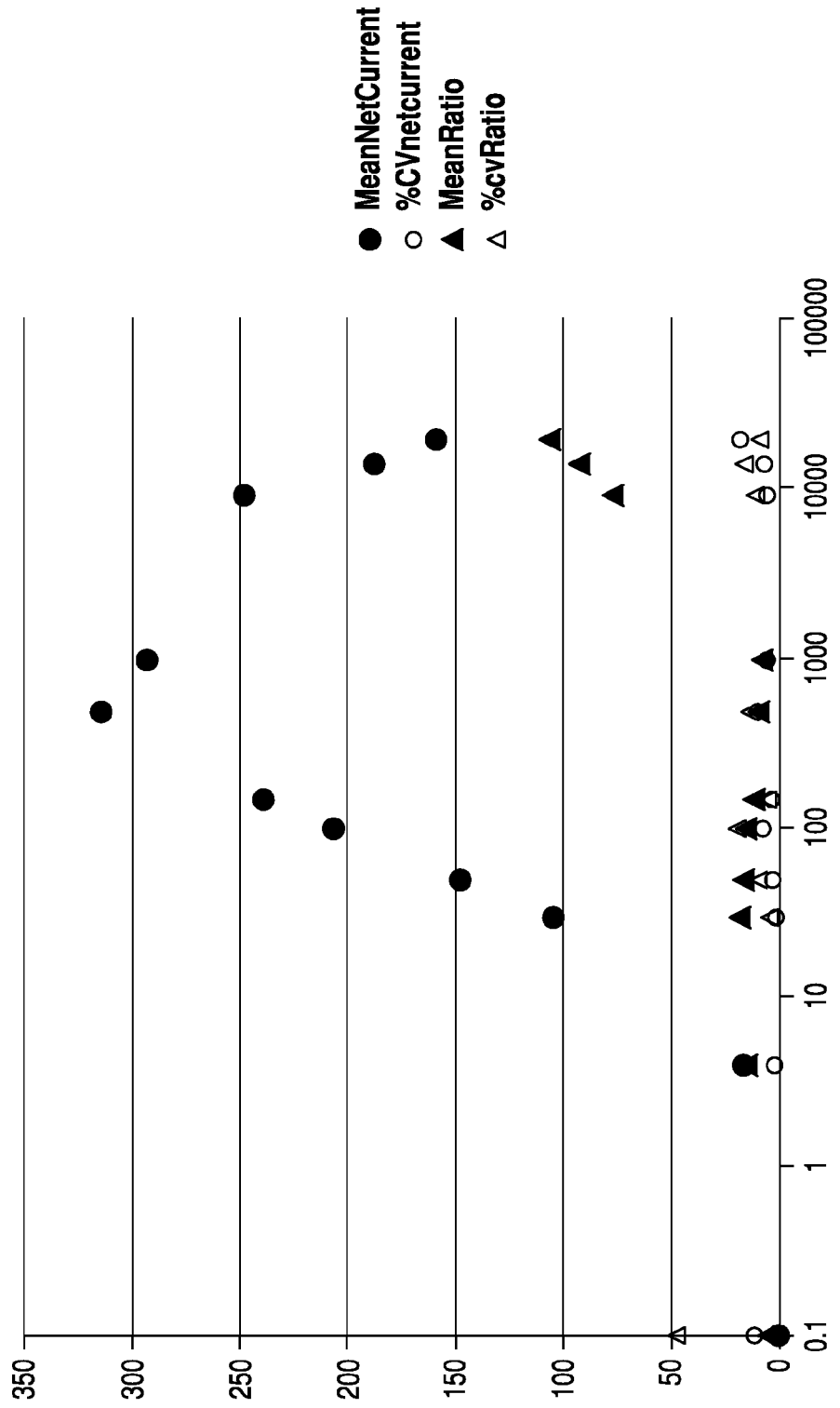
Figure 20:
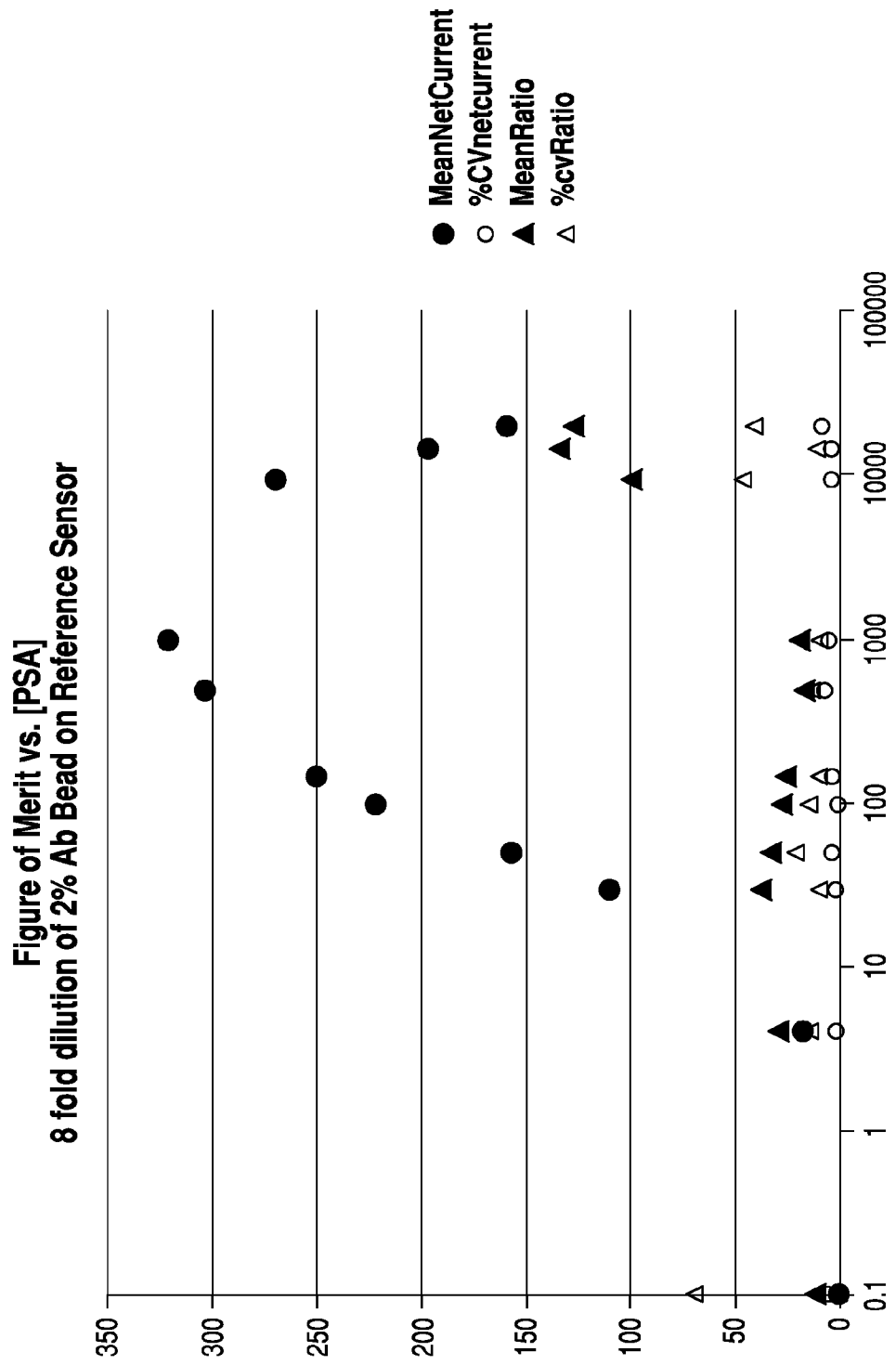

FIG. 17 illustrates the use of the sensor response ratio as a viable embodiment for hook detection. Here A is the Analyte sensor bearing a microparticle print coated with anti-analyte antibody. The reference sensor, R, bears an attenuated reagent of microparticles coated with a much lower coverage of anti-analyte antibody. FIGS. 18, 19, and 20 provide data for PSA analysis in accordance with these aspects of the present invention. The assays included using three different "attenuated" reference reagents in two-sensor devices consisting of an Analyte (A) sensor and a Reference (R) sensor. Each of these reagents was prepared by diluting a polystyrene microparticle co-coated with a 2:98 anti-PSA:anti-HSA mixture (HSA is anti-human serum albumin) with a microparticle coated with only anti-HSA. Each figure exhibits the primary immunosensor response (microparticle coated with anti-PSA, i.e., A from FIG. 17) and the value of the response ratio (A/R from FIG. 17) as a function of PSA concentration. In each instance, the primary dynamic range of the device is in range of analyte concentrations from 0 to 100 ng/mL of PSA. At higher concentrations, the primary sensor is insensitive to changes in concentrations until approximately 10,000 ng/mL whereupon further increases in concentration results in diminished sensor response owing to the hook effect. In the absence of information beyond the primary sensor signal, signals at higher concentrations could be misinterpreted as being below 100 ng/mL, a classic problem in traditional immunoassays.

More specifically, FIG. 18 illustrates data from a reference sensor with two-fold dilution of 2:98 anti-PSA:anti-HAS (with anti-HAS microparticle). FIG. 19 illustrates data from a reference sensor with four-fold dilution of 2:98 anti-PSA:anti-HSA (with anti-HSA microparticle). FIG. 20 illustrates data from a reference sensor with eight-fold dilution of 2:98 anti-PSA:anti-HSA (with anti-HSA microparticle). It should be evident to those of ordinary skill in the art that these three figures illustrate that as the reference reagent is further attenuated, i.e., greater dilution with anti-HSA microparticle), the value of the A/R ratio increases owing to the property that reference sensors containing lower amounts of the analyte-specific antibody will generate lower signals. Also shown in the plots of the three figures (hollow symbols) is the imprecision (as % CV) of the A and A/R figures of merit. It can be seen from comparison of the three figures that the activity (in this case controlled by dilution of the reagent) of the reference reagent can be used to tune/adjust the magnitude as well as the imprecision of the response ratio A/R used to detect a hook effect region.

The two sensor arrangements described herein allow for a distinction between a primary signal (A) within the dynamic range of the assay (0 to 100 ng/mL, low value of the A/R response ratio) and one in the hook effect region (high value of A/R). There may be a condition of such high analyte concentration that both sensors are saturated to the extent that no signal is observed at either sensor; in this condition it is no longer possible to distinguish between zero analyte and high analyte. In this case, the value of the two sensor arrangement remains in its ability to extend the dynamic range of analyte concentrations that can be tolerated from, for example, 0 to 10,000 ng/mL to 0 to 100,000 ng/mL (before both sensors report no signal and erroneously, zero analyte concentration). The actual concentration of analyte at which this happens should be determined for each specific measurement system.

While the invention has been described in terms of various preferred embodiments, those skilled in the art will recognize that various modifications, substitutions, omissions and changes can be made without departing from the spirit of the present invention. It is intended that the scope of the present invention be limited solely by the scope of the following claims. In addition, it should be appreciated by those skilled in the art that a plurality of the various embodiments of the invention, as described above, may be coupled with one another and incorporated into a single reader device.

We claim:

1. A system for identifying a hook effect in an immunoassay, the system comprising:

a primary sensor comprising first immobilized antibodies and configured to generate a first signal based on a presence or absence of a target analyte in a sample;

an attenuated sensor comprising second immobilized antibodies at a reduced concentration relative to a concentration of the first immobilized antibodies on the primary sensor and configured to generate a second signal based on the presence or absence of the target analyte in the sample; and a processor configured to determine a presence of a hook effect in the immunoassay based on relative values of the first and second signals.

2. The system of claim 1, wherein the first immobilized antibodies comprise a first affinity for the target analyte and the second immobilized antibodies comprise a second affinity for the target analyte, the first affinity being different from the second affinity.

3. The system of claim 1, wherein the first and second immobilized antibodies are the same antibodies.

4. The system of claim 1, wherein the first and second immobilized antibodies are immobilized on microparticles.

5. The system of claim 4, wherein the microparticles are adsorbed over the primary sensor and the attenuated sensor.

6. The system of claim 5, wherein the first and second immobilized antibodies comprise at least one antibody specific to the target analyte.

7. The system of claim 6, wherein the microparticles adsorbed over the attenuated sensor comprise the second immobilized antibodies and a co-absorbate.

8. The system of claim 7, wherein the microparticles adsorbed over the primary sensor do not comprise the co-absorbate.

9. The system of claim 7, wherein the co-absorbate dilutes surface activity of the second immobilized antibodies on the microparticles adsorbed over the attenuated sensor.

10. The system of claim 7, wherein the presence of the co-absorbate on the microparticles over the attenuated sensor provides the reduced concentration of the second immobilized antibodies relative to the concentration of first immobilized antibodies.

11. The system of claim 7, wherein the co-absorbate comprises non-specific antibodies and/or proteins.

12. The system of claim 11, wherein the non-specific antibodies comprise mouse IgG or goat IgG.

13. The system of claim 11, wherein the proteins comprise bovine serum albumin (BSA) or human serum albumin (HSA).

14. The system of claim 1, wherein the processor is further configured to determine a concentration of the target analyte based on the presence of the hook effect and the relative values of the first and second signals.

15. The system of claim 1, further comprising at least one additional sensor comprising third immobilized antibodies at a different concentration relative to the concentrations of the first and second immobilized antibodies and configured to generate a third signal based on the presence or absence of the target analyte in the sample,
wherein the processor is further configured to determine a concentration of the target analyte based on the presence of the hook effect and relative values of the first, second, and third signals.

16. An immunosensor system for identifying a hook effect in an immunoassay, the immunosensor system comprising:
a primary immunosensor comprising a first immobilized antibody and configured to generate a first signal based on a sandwich between the first immobilized antibody, a target analyte, and a labeled antibody;
an attenuated immunosensor comprising a second immobilized antibody at a reduced concentration relative to a concentration of the first immobilized antibody and configured to generate a second signal based on a sandwich between the second immobilized antibody, the target analyte, and the labeled antibody; and
a processor configured to determine a presence of a hook effect in the immunoassay based on relative values of the first and second signals.

17. The immunosensor system of claim 16, wherein the first immobilized antibodies comprise a first affinity for the target analyte and the second immobilized antibodies comprise a second affinity for the target analyte, the first affinity being different from the second affinity.

18. The immunosensor system of claim 16, wherein the first and second immobilized antibodies are the same antibodies.

19. The immunosensor system of claim 16, wherein the primary immunosensor and the attenuated immunosensor are electrochemical sensors.

20. The immunosensor system of claim 16, wherein the labeled antibody is labeled with alkaline phosphatase (ALP).

21. The immunosensor system of claim 16, wherein the labeled antibody is labeled with alkaline phosphatase (ALP) and the first and second signals are generated at the primary immunosensor and the attenuated immunosensor respectively from an electroactive species with a phosphate moiety that is cleaved by the ALP.

22. The immunosensor system of claim 16, wherein the primary immunosensor and the attenuated immunosensor are disposed in a disposable cartridge that is configured to perform the immunoassay to determine a presence of the target analyte in a sample.

23. The immunosensor system of claim 22, wherein the sample comprises a blood sample.

24. The immunosensor system of claim 16, wherein the target analyte is selected from the group consisting of: troponin I, troponin T, creatine kinase myocardial band (CKMB), procalcitonin, beta human chorionic gonadotropin (bHCG), human chorionic gonadotropin (HCG), N-terminal pro brain natriuretic peptide (NTproBNP), pro brain natriuretic peptide (proBNP), brain natriuretic peptide (BNP), myoglobin, parathyroid hormone, d-dimer, neutrophil gelatinase-associated lipocalin (NGAL), galectin-3, and prostate specific antigen (PSA).

25. The immunosensor system of claim 16, wherein the second immobilized antibody is provided at the attenuated immunosensor at less than about 5% of a binding capacity of the first immobilized antibody provided at the primary immunosensor.

26. The immunosensor system of claim 16, wherein the processor is configured to determine the lack of the hook effect when the second signal from the attenuated immunosensor is high and the first signal from the primary immunosensor is commensurately high.

27. The immunosensor system of claim 16, wherein the processor is configured to determine the presence of the hook effect when the second signal from the attenuated immunosensor is low and the first signal from the primary immunosensor is high.

28. The immunosensor system of claim 16, wherein the first and second immobilized antibodies have an affinity constant in a range of about $1 \times 10^{-7}$ to $1 \times 10^{-15}$.

29. The immunosensor system of claim 16, wherein the first and second immobilized antibodies are immobilized on microparticles having a diameter in a range of about 0.01-5.0 μm.

30. The immunosensor of claim 16, wherein:
the primary immunosensor further comprises a first electrode and a first polyvinyl alcohol layer (PVA), the first PVA layer being disposed between the first electrode and the first immobilized antibody; and
the attenuated immunosensor further comprises a second electrode and a second PVA layer, the second PVA layer being disposed between the second electrode and the second immobilized antibody.

31. An immunosensor system comprising:
- a plurality of immunosensors, wherein each immunosensor of the plurality of immunosensors comprises a different concentration of an immobilized antibody specific to an analyte of interest, and each immunosensor is configured to generate a signal based on a sandwich between the immobilized antibody, the analyte of interest, and a labeled antibody; and
- a processor configured to determine a presence of a hook effect in an immunoassay based on relative values of each generated signal.

32. The immunosensor system of claim 31, wherein the processor is further configured to determine a concentration of the analyte of interest based on the presence of the hook effect and the relative values of each generated signal.

33. A method for identifying a hook effect in an immunoassay, the method comprising:
- providing a sample to a primary sensor comprising first immobilized antibodies;
- generating a first signal from the primary sensor based on a presence or absence of a target analyte in the sample;
- providing the sample to an attenuated sensor comprising second immobilized antibodies provided at a reduced concentration relative to a concentration of the first immobilized antibodies;
- generating a second signal from the attenuated sensor based on the presence or absence of the target analyte in the sample;
- determining a ratio of the first and the second signals based on relative values of the first and second signals; and
- determining a presence or absence of a hook effect in the immunoassay based on the determined ratio.

34. The method of claim 33, further comprising determining a concentration of the target analyte based on the presence or absence of the hook effect and the relative values of the first and second signals.

35. The method of claim 33, further comprising:
- providing the sample to at least one additional sensor comprising third immobilized antibodies at a different concentration relative to the concentrations of the first and second immobilized antibodies;
- generating a third signal based on the presence or absence of the target analyte in the sample; and
- determining a concentration of the target analyte based on the presence or absence of the hook effect and relative values of the first, second, and third signals.

36. A method of using an attenuated immunosensor for identifying a hook effect in an immunoassay for a target analyte, the method comprising:
- applying a sample to a primary immunosensor comprising a first immobilized antibody;
- generating a first signal from the primary immunosensor based on a sandwich between the first immobilized antibody, the target analyte, and a labeled antibody;
- applying the sample to the attenuated immunosensor comprising a second immobilized antibody provided at a reduced concentration relative to a concentration of the first immobilized antibody;
- generating a second signal from the attenuated immunosensor based on a sandwich between the second immobilized antibody, the target analyte, and the labeled antibody;
- computing relative values of the first and second signals;
- determining a ratio of the first and second signals based on the relative values of the first and second signals; and
- determining a presence or absence of a hook effect in the immunoassay based on the determined ratio.

* * * * *